United States Patent [19]

Rohr

[11] Patent Number: 5,445,971
[45] Date of Patent: Aug. 29, 1995

[54] MAGNETICALLY ASSISTED BINDING ASSAYS USING MAGNETICALLY LABELED BINDING MEMBERS

[75] Inventor: Thomas E. Rohr, Gurnee, Ill.

[73] Assignee: Abbott Laboratories, Abbott Park, Ill.

[21] Appl. No.: 348,780

[22] Filed: Dec. 1, 1994

Related U.S. Application Data

[63] Continuation of Ser. No. 161,376, Dec. 2, 1993, abandoned, which is a continuation-in-part of Ser. No. 854,151, Mar. 20, 1992, abandoned.

[51] Int. Cl.[6] .................. G01N 33/546; G01N 33/553
[52] U.S. Cl. .................................... 436/526; 435/291; 436/528; 436/534; 436/806; 422/236; 209/214
[58] Field of Search ............... 435/291; 436/526, 518, 436/528, 534, 806; 422/236; 209/214; 210/222, 223, 695

[56] References Cited

U.S. PATENT DOCUMENTS 5,252,493 10/1993 Fujiwara et al. .................. 436/526

FOREIGN PATENT DOCUMENTS 8802118 7/1988 WIPO .

Primary Examiner—Toni R. Scheiner
Assistant Examiner—Susan C. Wolski
Attorney, Agent, or Firm—Mark C. Bach

[57] ABSTRACT

The present invention provides devices for performing binding assays. Such devices comprise (i) a reaction vessel where unbound and immobilized magnetically-labeled reagent are produced in relation to the amount of said analyte in said test sample; (ii) a separation means for partitioning said immobilized magnetically-labeled reagent and said bound magnetically-labeled reagent; (iii) a magnetic field generator means for the application of a magnetic field to said magnetically-labeled reagent; and (iv) a measurement means to assess the effect of said magnetic field on said magnetically-labeled reagent as a measure of the presence or amount of said analyte in said test sample. The device provided by the instant invention can run, for example, direct indirect, competitive, inhibition and sandwich assay formats.

2 Claims, 12 Drawing Sheets

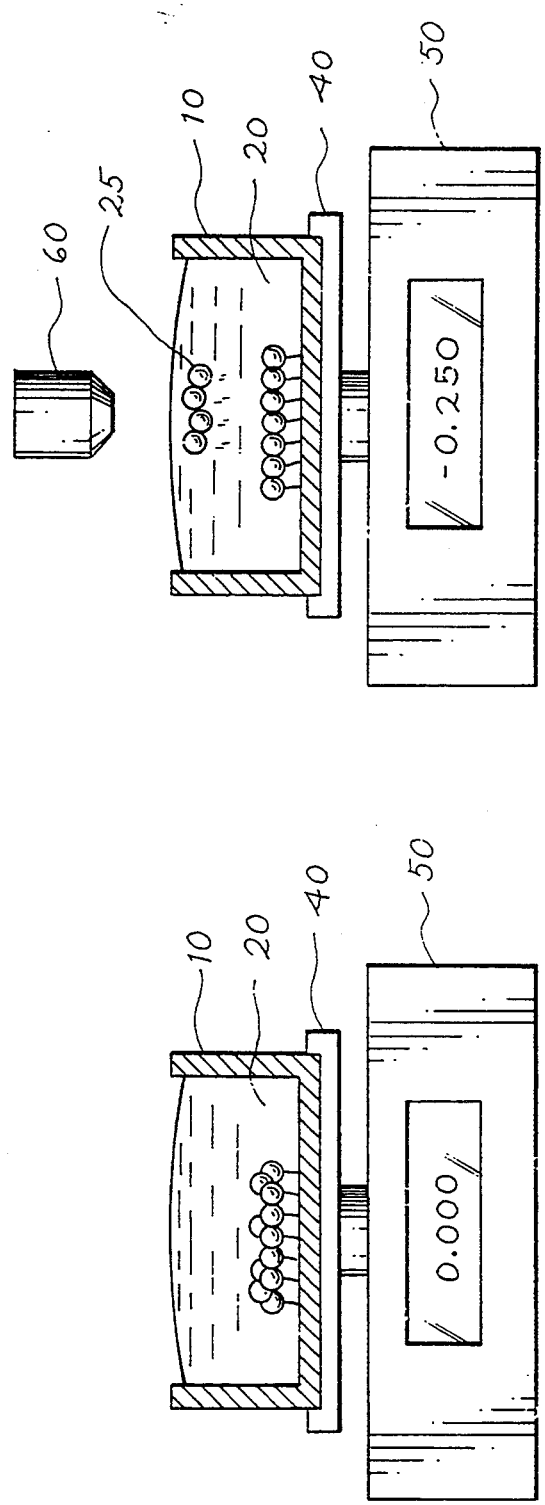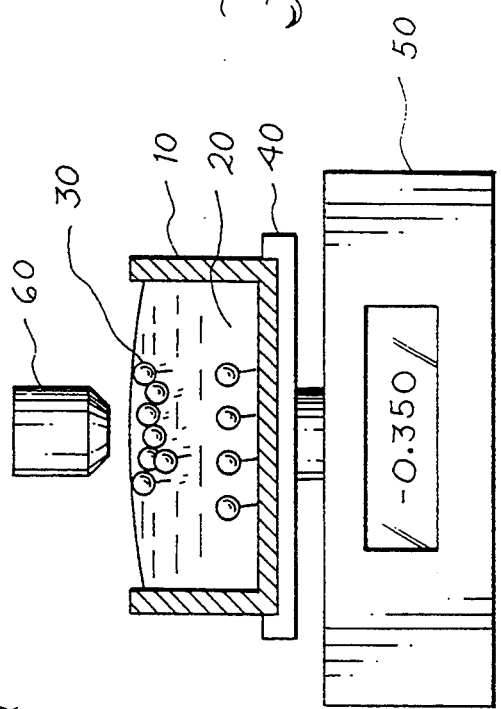
Fig. 12a
Fig. 12b
Fig. 12c

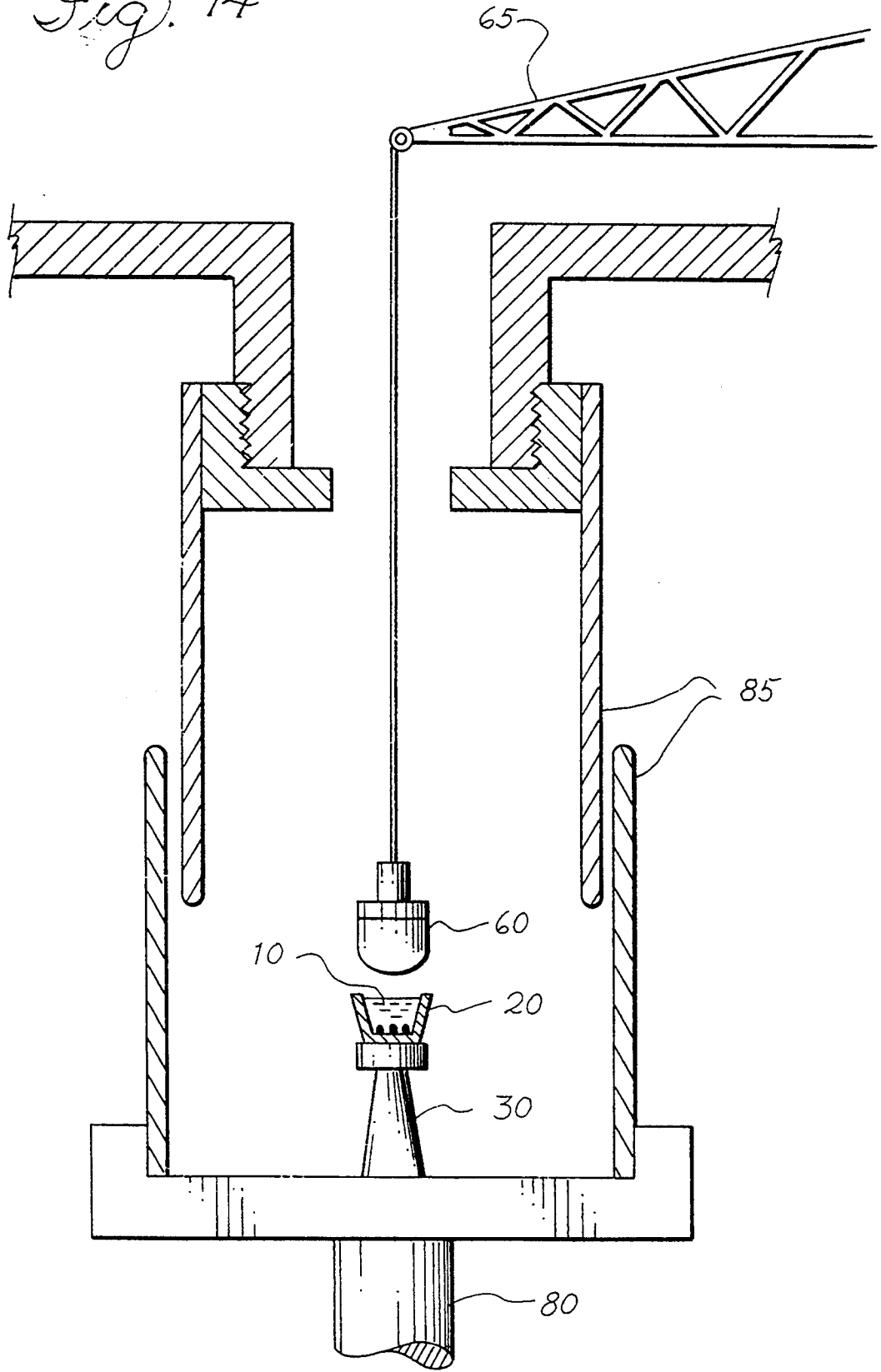

MAGNETICALLY ASSISTED BINDING ASSAYS USING MAGNETICALLY LABELED BINDING MEMBERS

This application is a continuation of application Ser. No. 08/161,376 filed on Dec. 2, 1993, now abandoned.

Application Ser. No. 08/161,376 is a continuation-in-part of U.S. patent application Ser. No. 07/854,151, filed Mar. 20, 1992, now abandoned.

FIELD OF THE INVENTION

This invention relates to a method for determining the presence or amount of analyte in a test sample using a detectable label attached to a binding member. In particular, the invention relates to the use of magnetically-attractable materials as the detectable label.

BACKGROUND OF THE INVENTION

Diagnostic assays have become an indispensable means for detecting analytes in test samples by using the mutual reaction between the analyte and a specific binding member for the analyte, such as the immunoreaction between an antigen and the antibody to that antigen. Typically, detectable tags or labels attached to antibodies, which in turn bind to the analyte of interest, are employed in such diagnostic assays, wherein the detection of the resultant labeled antibody/analyte complex, or of the labeled antibody which remains unbound, is used to indicate the presence or amount of analyte in the test sample.

Two commonly used binding assay techniques are the radioimmunoassay (RIA) and the enzyme immunoassay (EIA), both of which employ a labeled binding member. The RIA uses a radioactive isotope as the detectable tag or label attached to a binding member. Because the radioactive isotope can be detected in very small amounts, it can be used to detect or quantitate small amounts of analyte. However, substantial disadvantages associated with the RIA include the special facilities and extreme caution that are required in handling radioactive materials, the high costs of such reagents, and their unique disposal requirements.

The EIA uses an enzyme as the detectable tag or label attached to a binding member, wherein the enzymatic activity of the enzyme is used to detect the immunoreaction. While the EIA does not have the same disadvantages as the RIA, EIA techniques typically require the addition of substrate materials to elicit the detectable enzyme reaction. Enzyme substrates are also often unstable and have to be prepared just prior to use or be stored under refrigeration. In addition, enzyme labels may be difficult to purify and conjugate to binding members, and may be unstable during storage at room temperature. Enzyme immunoassays are also unsatisfactory in that the methods typically require complex incubations, multiple liquid additions and multiple wash steps. Moreover, even under refrigerated conditions, enzymes are unstable.

More recently, assay techniques using metallic sol particles as visual labels have been developed. In these techniques, a metal (e.g., gold, silver, platinum), a metal compound, or a nonmetallic substance coated with a metal or a metal compound, is used to form an aqueous dispersion of particles. Generally, the binding member to be labeled is coated onto the metal sol particles by adsorption, and the particles are captured or aggregated in the presence of analyte. Although the metal sol particles have the advantage of producing a signal that is visually detectable as well as measurable by an instrument, they, nevertheless, are difficult to quantitatively measure. The metallic particles also have a limited color intensity, and therefore limited sensitivity in some assays. In addition, the surfaces of inorganic metallic colloid particles, such as gold, do not readily accept the covalent attachment of binding members. Thus, during use in a binding assay, care must be taken so that the adsorbed binding members are not removed from the inorganic particles through the combination of displacement by other proteins or surface active agents and the shear forces which accompany washing steps used to remove non-specifically bound material. Sol particles can be difficult to coat without inducing aggregation, may aggregate upon storage and may aggregate upon the addition of buffers or salts. Furthermore, such particulate labels are difficult to concentrate, may aggregate during use and are difficult to disperse.

Other label materials include chemiluminescent and fluorescent substances. Non-metallic particles, such as dyed or colored latex and selenium particles have also been used as visual labels.

Prior to the present invention, magnetic particles and magnetic fields have generally been used as means to remove or position an analyte component of a test sample. For example, U.S. Pat. Nos. 4,070,246 and 3,985,649 describe the use of binding members attached to ferromagnetic particles, whereby the binding member forms a complex with the analyte of interest, and the resulting complex is removed from the reaction mixture by means of a magnetic field. Alternatively, U.S. Pat. No. 3,933,997 describes the use of magnetic particles and a magnetic field as a means of concentrating a radioactive material on a test substance. U.S. Pat. No. 4,219,335 describes the use of magnetic particles which have characteristics capable of affecting electrical resistance, wherein a capacitance measurement will reveal whether the particles are present on a surface. However, the effect of the magnetic field on the magnetic particles has no relation to the presence or amount of analyte in the test sample.

SUMMARY OF THE INVENTION

The present invention advantageously uses a magnetically-attractable material as a detectable label in binding assays. The magnetic label is subjected to a magnetic field and the label, in turn, displays a resultant force or movement as a result of the application of the magnetic field. According to the present invention, the extent of the force or movement is modulated by an analyte that may be present in a test sample. Because the presence or amount of analyte in a test sample is responsible for the magnitude of the force exerted or the amount of movement displayed by the attractable material, the effect of the magnetic field on the magnetically-attractable label can be used as a measure of the presence or amount of analyte in a test sample.

According to the present invention, a method of determining the presence or amount of analyte in a test sample comprises contacting a test sample with a solid-phase reagent and a magnetically-labeled reagent. The solid-phase reagent comprises a first binding member attached to a solid phrase, and the magnetically-labeled reagent comprises a second binding member attached to a magnetically-attractable label. The first binding member is selected to bind (i) the analyte or (ii) the second binding member, and the second binding member is selected to bind (i) the analyte or (ii) the first binding member, to thereby provide for competitive and sandwich immunoassay formats.

According to another method of the invention, determining the presence or amount of analyte in a test sample comprises contacting a test sample with a solid-phase reagent, a magnetically-labeled reagent and at least one ancillary binding member. The solid-phase reagent comprises a first binding member attached to a solid phase, and the magnetically-labeled reagent comprises a second binding member attached to a magnetically-attractable label. The first and second binding members are selected to bind either (i) at least one ancillary binding member or (ii) the analyte. The ancillary binding member is selected to bind (i) the analyte, (ii) the first binding member, or (iii) the second binding member, to thereby provide for competitive and sandwich immunoassay formats.

According to the method of the present invention, there is a partitioning of the magnetically-labeled reagent between unbound magnetically-labeled reagent and magnetically-labeled reagent that becomes bound or immobilized to the solid-phase reagent in relation to the amount of analyte present in the test sample. The unbound magnetically-labeled reagent can be separated from the magnetically-labeled reagent bound to the solid-phase reagent prior to or during the application of a magnetic field to the magnetically-labeled reagent. The magnetic field causes the magnetically-labeled reagent to respond in a manner that is related to the presence or amount of analyte present in the test sample. By detecting the extent of the magnetically-labeled reagent's response, the presence or amount of the analyte in a test sample can be determined. The extent of the magnetically-labeled reagent's response can be manifested in many measurable forms which can be detected using any means suitable for detecting the magnetically-labeled reagent's response to the magnetic field.

The present invention also provides devices for determining the presence or amount of an analyte in a test sample. Such devices comprise (i) a reaction vessel where unbound and immobilized magnetically-labeled reagent are produced in relation to the amount of analyte in the test sample; (ii) a separation means for partitioning the immobilized magnetically-labeled reagent and the unbound magnetically-labeled reagent; (iii) a magnetic field generator means for the application of a magnetic field to the magnetically-labeled reagent; and (iv) a measurement means to assess the effect of the magnetic field on the magnetically-labeled reagent as a measure of the presence or amount of the analyte in the test sample. It will be understood, of course, that the magnetic field generator means can also serve as the separation means and that suitable magnetic field generator means comprise permanent magnets and electromagnets.

BRIEF DESCRIPTION OF THE DRAWINGS

FIGS. 5a–b illustrates the measurement of the attractive force of unbound or free magnetically-labeled reagent.

FIGS. 12a–c sequentially illustrate a schematic view of the measurement means for the determination of the strength of associations between complementary binding members.

FIG. 14 is a schematic view of the magnetically assisted detection of magnetically-labeled reagent using a field generator means suspended from a balance means.

DETAILED DESCRIPTION OF THE INVENTION

Figure 2:
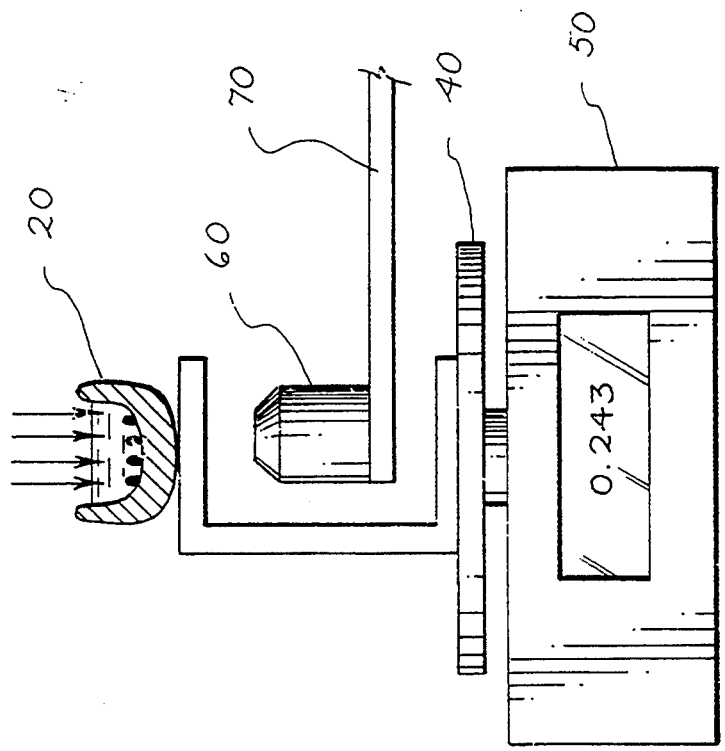
FIG. 2 is a schematic view of a balance means in operation for the magnetically assisted detection of a magnetically-labeled reagent.

The following definitions are applicable to the invention:

Definitions

The term "test sample", as used herein, refers to a material suspected of containing the analyte. The test sample can be used directly as obtained from the source or following a pre-treatment to modify the character of the sample. The test sample can be derived from any biological source, such as a physiological fluid including, but not intended to be limited to blood, saliva, ocular lens fluid, cerebral spinal fluid, sweat, urine, milk, ascites fluid, mucous, synovial fluid, peritoneal fluid, amniotic fluid and the like; fermentation broths; cell cultures; chemical reaction mixtures and the like.

The test sample can be pretreated prior to use, such as preparing plasma from blood, diluting viscous fluids, and the like. Methods of treatment can involve filtration, distillation, concentration, inactivation of interfering components, and the addition of reagents. In addition to biological or physiological fluids, other liquid samples can be used such as water, food products and the like for the performance of environmental or food production assays. In addition, a solid material suspected of containing the analyte can be used as the test sample. In some instances, it may be beneficial to modify a solid test sample to form a liquid medium or to release the analyte.

The term "binding member", as used herein, refers to a member of a binding pair, i.e., two different molecules wherein one of the molecules specifically binds to the second molecule through chemical or physical means. In addition to the well-known antigen and antibody binding pair members, other binding pairs include, but are not intended to be limited to, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), sugar and boronic acid, and similar molecules having an affinity which permits their association in a binding assay. Furthermore, binding pairs can include members that are analogs of the original binding member, for example an analyte-analog or a binding member made by recombinant techniques or molecular engineering. If the binding member is an immunoreactant it can be, for example, an antibody, antigen, hapten, or complex thereof, and if an antibody is used, it can be a monoclonal or polyclonal antibody, a recombinant protein or antibody, a chimeric antibody, a mixture(s) or fragment(s) thereof, as well as a mixture of an antibody and other binding members. The details of the preparation of such antibodies, peptides and nucleotides and their suitability for use as binding members in a binding assay are wellknown to those skilled-in-the-art.

The term "analyte" or "analyte of interest", as used herein, refers to the compound or composition to be detected or measured and which has at least one epitope or binding site. The analyte can be any substance for which there exists a naturally occurring binding member or for which a binding member can be prepared. Analytes include, but are not intended to be limited to, toxins, organic compounds, proteins, peptides, microorganisms, amino acids, carbohydrates, nucleic acids, hormones, steroids, vitamins, drugs (including those administered for therapeutic purposes as well as those administered for illicit purposes), virus particles and metabolites of or antibodies to any of the above substances. For example, such analytes include, but are not intended to be limited to, ferritin; creatinine kinase MIB (CK-MB); digoxin; phenytoin; phenobarbitol; carbamazepine; vancomycin; gentamycin; theophylline; valproic acid; quinidine; leutinizing hormone (LH); follicle stimulating hormone (FSH); estradiol, progesterone; IgE antibodies; vitamin B2 micro-globulin; glycated hemoglobin (Gly. Hb); cortisol; digitoxin; N-acetyl-procainamide (NAPA); procainamide; antibodies to rubella, such as rubella-IgG and rubella-IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti hepatitis B core antigen IgG and IgM (Anti-HBC); human immune deficiency virus 1 and 2 (HTLV); hepatitis B e antigen (HBeAg); antibodies to hepatitis B e antigen (Anti-HBe); thyroid stimulating hormone (TSH); thyroxine (T4); total triiodothyronine (Total T3); free triiodothyronine (Free T3); carcinoembryoic antigen (CEA); and alpha fetal protein (AFP); and drugs of abuse and controlled substances, including but not intended to be limited to, amphetamine; methamphetamine; barbiturates such as amobarbital, secobarbital, pentobarbital, phenobarbital, and barbital; benzodiazepines such as librium and valium; cannabinoids such as hashish and marijuana; cocaine; fentanyl; LSD; methapualone; opiates such as heroin, morphine, codeine, hydromorphone, hydrocodone, methadone, oxycodone, oxymorphone and opium; phencyclidine; and propoxyhene. The term "analyte" also includes any antigenic substances, haptens, antibodies, macromolecules and combinations thereof.

The term "analyte-analog", as used herein, refers to a substance which cross-reacts with an analyte-specific binding member, although it may do so to a greater or a lesser extent than does the analyte itself. The analyte-analog can include a modified analyte as well as a fragmented or synthetic portion of the analyte molecule, so long as the analyte-analog has at least one epitopic site in common with the analyte of interest. An example of an analyte-analog is a synthetic peptide sequence which duplicates at least one epitope of the whole-molecule analyte so that the analyte-analog can bind to an analyte-specific binding member.

The term "magnetically-labeled reagent", as used herein, refers to a substance involving a magnetically-attractable label attached to a binding member. The attachment may be affected by covalent or non-covalent binding means, linking arms, and the like. However, the method of attachment is not critical to the present invention. Upon the application of a magnetic field, the magnetically-attractable label allows the reagent to produce a detectable response that will be directly or indirectly related to the amount of analyte in the test sample. The binding member component of the reagent may be selected to directly bind the analyte or to indirectly bind the analyte by means of an ancillary specific binding member, which is described in greater detail hereinafter. Magnetically-labeled reagents may be attached to ancillary specific binding members before, during or after contacting the magnetically-labeled reagent with the test sample and/or other assay reagents. The terms "binding member attached to a magnetically-attractable particle", "binding member attached to a magnetic material", "binding member attached to a magnetic label", "binding member attached to a magnetically-responsive label" and similar terms are interchangeable and are used to refer to the main characteristic of the magnetically-labeled reagents of the present invention, i.e., the label produces a detectable response when placed in the vicinity of a magnetic field.

The term "solid phase", as used herein, refers to any material to which analyte, analyte complexes or assay reagents become bound and from which unreacted assay reagents, test sample or test solutions can be separated. The solid phase generally has a binding member immobilized on or in its surface to form a "solid-phase reagent", that allows the immobilization of the analyte, the magnetically-labeled reagent or another assay reagent. Binding members which are immobilized in or on the solid phase may be selected to directly bind the analyte or to indirectly bind the analyte by means of an ancillary specific binding member which can be immobilized to the solid-phase reagent before, during, or after contacting the solid-phase reagent with the test sample and/or other assay reagents.

It will be understood, of course, that the solid phase may comprise multiple components and that the immobilized binding member can be bound directly to any or all components of the solid phase. For example, a multiple component solid phase can include a solid-phase reagent that is physically entrapped or retained and immobilized within a second or supplementary component of the solid phase by a physical, chemical or biochemical means. As a further example, an analyte-specific binding member can be attached to insoluble microparticles which are subsequently retained by a porous material. By "retained" it is meant that the microparticles, once on the porous material, are not capable of substantial movement to positions elsewhere within the porous material. A first solid phase component, which itself can be a solid-phase reagent, can be retained by a supplementary component of the solid phase before, during or after contacting the first solid phase component with the test sample and/or other assay reagents. In most embodiments, however, the binding member is bound or attached to a single solid phase component prior to contacting the thusly formed solid-phase reagent with the test sample or other assay reagents.

The term "ancillary binding member", as used herein, refers to any member of a binding pair which is used in the assay in addition to the binding members of the magnetically-labeled reagent or solid-phase reagent. For example, in instances where the analyte itself cannot directly attach to the magnetically-labeled reagent, an ancillary binding member can be capable of binding the magnetically-labeled reagent to the analyte of interest. As it will be understood, of course, one or more ancillary binding members can be used in an assay and such ancillary binding member(s) can be attached to the magnetically-labeled reagent or solid-phase reagent either before, during or after the magnetically-labeled reagent or solid-phase reagent is contacted with a test sample or other assay reagent. The ancillary binding member can be incorporated into the assay device or it can be added to the device as a separate reagent solution.

Description of the Invention

When a magnetically-responsive material is placed under the influence of a magnetic field, the material will tend to move toward or away from the region where the magnetic field is the strongest. For example, a paramagnetic material, such as ferrite, will be attracted to the magnetic field while a diamagnetic material, such as polystyrene, will move away from the magnetic field. The extent of the response of such magnetically-responsive materials can be used as a measure of the amount of material present. The present invention results from the unexpected and surprising discovery that, when a magnetically-responsive material is used as a label in a binding assay, it is possible to detect the presence or amount of either or both of the free or bound label by measuring the extent of the response resulting from the label's reaction to an applied magnetic field. The magnetic label's response to a magnetic field can manifest itself in ways such as, for example, a detectable movement of the magnetically-responsive material or a detectable resultant force exerted by the magnetically-responsive material. Furthermore, the strength of the force or the extent of movement bears a definite relationship to the amount of the bound or free magnetically-attractable label which thereby permits a determination of the presence or amount of an analyte in the test sample.

Conventional heterogeneous binding assay formats require vigorous washing of the solid phase to separate bound and unbound labeled reagent and to suppress the nonspecific binding of materials to the solid phase. Such wash steps complicate the assay protocol and restrict the assay to the use of binding pair members having high affinity, i.e., a binding strength that will withstand such physical manipulation. Conversely, the present invention avoids the need for complex washing steps in binding assays because unbound or non-specifically bound label can be separated from the reaction mixture by the application of a first magnetic field prior to the detection of specifically bound label by means of a second magnetic field. The high degree of control that is possible over the magnetic field permits the use of a first field that is suitable to separate free or non-specifically bound label from a reaction mixture without affecting specifically bound label. In turn, this permits the use of lower affinity binding members whose binding will not be significantly affected by the first magnetic field.

In conventional particle agglutination assays, binding members of low affinity can be used because several binding sites on each member can cooperate to give high avidities, and the absence of wash steps allows weak associations to be maintained while simplifying the assay format. Signal amplification results from the fact that the interaction of a few binding sites can cause the aggregation of binding members several orders of magnitude greater in size and mass than the original members, and thereby provide a macroscopic change which can be interpreted visually. However, particle agglutination assays are often difficult to interpret, do not yield quantitative results, and are not readily amenable to automation.

The present invention solves the aforementioned problems of conventional heterogeneous and agglutination assays by placing the magnetic label in a magnetic field, and measuring the consequences of the magnetic force exerted upon the label to provide a qualitative or quantitative assay readout. The force affect of the magnetic field upon the magnetic label enhances the detection of the captured or aggregated magnetic label while suppressing non-specific interference from any nonmagnetic substances. For example, the nonspecific binding of extraneous substances to the solid phase will not interfere with the analyte determination because the force affect of the magnetic label in a magnetic field is measured, as opposed to determining the total weight of the resulting binding complex or reagents adhering to the solid phase. Force enhancements approaching about three orders of magnitude have been achieved by the application of a magnetic field and the detection of the resultant force affect on the magnetic label in that field. In comparison to the detection of weight changes due to binding reactions (e.g., the detection of the weight of bound analyte as is determined by conventional gravimetric analyses), the present invention provides binding assay signal enhancements of about nine orders of magnitude and is sufficient to detect analyte concentrations in the femtomolar ($10^{-15}$ mole or one quadrillionth mole) range. In this regard, small levels of force can be readily determined using detection means which include, but are not intended to be limited to, electronic balances; optical sensors; piezoelectric pressure sensing devices such as, for example, micromechanical silicon devices or electronic chips; vibrating fiber devices; coils which produce a field which is disrupted by the presence of a magnetically-responsive label such as, for example induction coils and the like; and cantilever beam devices including, but not intended to be limited to those used to sense force changes in an atomic force microscope; and the like. This enables very sensitive assays and obviates the need for amplification of the label as required in many conventional assays.

According to the present invention, the intensity of the magnetic field can be precisely manipulated by, for example, means of an electromagnetic or a movable permanent magnet. A field intensity can be chosen which is optimal for a particular assay and particular binding reagents, such that a field sufficient to remove unbound and non-specifically bound magnetic label can be applied without disrupting the associations formed between the binding members. This provides the opportunity to use binding members having lower binding affinities than those typically found in binding assays.

It is to be understood that the aforementioned advantages permit the assays to be readily adapted to computer control. In addition, the intensity of the magnetic field can be precisely manipulated to disrupt the associations formed between the binding members. Thus, the present invention also provides a means to evaluate the binding affinities or association constants of binding members.

(a) Assay Reagents

The selection of a particular composition of magnetic label material is not critical to the present invention. Preferably, the magnetically-attractable material can bind, carry or be modifiable so as to attach to a binding member which will in turn bind another assay reagent or a component present in a test sample. It is also preferred that the label be magnetically attractable to an extent which permits partitioning of the bound and unbound magnetically-labeled reagent and the production of a detectable response upon exposure to a magnetic field. For the purposes of the present invention, a material is magnetically responsive if it is influenced by the application of a magnetic field, such as, for example, if it is attracted or repulsed or has a detectable magnetic susceptibility or induction. A variety of different magnetically-labeled reagents can be formed by varying either the label component or the binding member component of the reagent. It will be understood, of course, that the choice involves consideration of the analyte to be detected and the desired optimization of the assay technique.

A wide variety of magnetically-attractable materials which are suitable for use as magnetic labels are commercially available or the production techniques therefor are well known in the art. The preferred characteristics of the magnetically-attractable label can be achieved by a wide variety of magnetic materials. Magnetically-attractable materials include, but are not intended to be limited to, ferromagnetic, ferrimagnetic, paramagnetic, superparamagnetic materials, and the like. The term "ferromagnetic" is generally used to describe materials which are attracted to a magnet and which typically become permanently magnetized upon exposure to a magnetic field. Ferromagnetic materials may also be reduced in particle size such that each of the particles is a single domain. In this state of subdivision, the ferromagnetic material may be referred to as "superparamagnetic", and characterized by the absence of any permanent measurable magnetization. Suitable magnetically-repulsed materials include, but are not intended to be limited to, diamagnetic materials such as, for example, organic polymers, including polystyrene, and the like.

Suitable ferromagnetic, ferrimagnetic, paramagnetic and superparamagnetic materials include, but are not intended to be limited to, metals such as iron, nickel, cobalt, chromium, manganese and the like; lanthanide series elements such as neodymiun, erbium and the like; alloys such as magnetic alloys of aluminum, nickel, cobalt, copper and the like; oxides such as ferric oxide ($Fe_3O_4$), $\gamma-$)ferric oxide ($\gamma-Fe_3O_4$), chromium oxide ($CrO_2$), cobalt oxide (CoO), nickel oxide ($NiO_2$), manganese oxide ($Mn_2O_3$) and the like; composite materials such as ferrites and the like; and solid solutions such as magnetite with ferric oxide and the like. Preferred magnetic materials are magnetite, ferric oxide ($Fe_3O_4$) and ferrous oxide ($Fe_2O_3$).

Suitable particle compositions include, but are not intended to be limited to, those particle types referred to in Table 1.

TABLE 1

| TYPE | FORM | COMPOSITION |
|---|---|---|
| Solid particles | | iron |
| | | iron oxide |
| | | core of magnetic material, coated with a metal oxide |
| | | colloidal magnetic particles containing magnetite or hematite and having a specific gravity of up to 8 and size range of less than 1 to 800 nanometers |
| Layered particles | magnetic material core with a nonmagnetic coating | a magnetic metal oxide core generally surrounded by a polymeric silane coat |
| | | a water-insoluble metal substrate coated with a condensation product of an aminobenzoic acid with an aldehyde, suitable for coupling to a compound having biological affinity |
| | magnetic material core with a nonmagnetic coating | a core formed of a single particle of magnetically-responsive material with a coating of a water-insoluble cross-linked polymeric material having reactive groups at the surface thereof |
| | | an organic polymer particle with a ferrite coating |
| | | a sphere of thermoplastic material with a magnetic material coating (on at least a portion of the core surface) |
| | | a metal-coated polyaldehyde microsphere |
| | | an inner core polymer particle (e.g., polystyrene) with a magnetically-responsive metal oxide/polymer coating evenly covering the inner core |
| | nonmagnetic core with a magnetic material layer and a nonmagnetic coating | an agarose-encapsulated metal-coated polyaldehyde microsphere |
| | | a thermoplastic resin bead (e.g., polystyrene, polyvinyl chloride, polyacrylate, nylon, etc.) with from 1–25% by weight of magnetically-responsive powder bound on the bead, and a |

TABLE 1-continued

| TYPE | FORM | COMPOSITION |
|---|---|---|
| Composite particles | magnetic material embedded within a nonmagnetic material | polymer coated thereon having functional groups to bind a biologically active component
iron-containing magnetic crystals (<1000 Å) incorporated within a glass and/or crystal structure
a copolymer matrix: 30–99% by weight, of at least one monoethylenic monomer which does not coordinate with a metal complex, 0.5–50% by weight, of at least one crosslinkable polyethylenic monomer which does not coordinate with a metal complex, and 0.5–30% by weight, of at least one nucleophilic monomer which can be coordinated with a metal complex, with encapsulated crystalites of a metal
magnetizable particles of a size less than 300 Å, encapsulated in an organpolysiloxane matrix
a particulate reaction product of a water-soluble form of iron and a water-soluble polymer having available coordination sites (free electron pair for a coordinate bond with a transition metal atom)
an organic, inorganic or synthetic polymer matrix containing a magnetically-attractable material
magnetizable particles of a size less than 300 Å, encapsulated in an organpolysiloxane matrix
a particulate reaction product of a water-soluble form of iron and a water-soluble polymer having available coordination sites (free electron pair for a coordinate bond with a transition metal atom)
an organic, inorganic or synthetic polymer matrix containing a magnetically-attractable material
a continuous phase of a water-insoluble polymeric matrix having dispersed (embedded) therein: a magnetically attractable material, and a particulate absorbent material (selected from charcoal, talc, ion exchange resins, Fuller's earth, silicon dioxide, oxides of zirconium or aluminum or titanium, porous glass, zeolites, natural or synthetic polymers, polymerized first or second antibodies or polymerized enzymes, cell surface antigens or receptors in a particulate form, subcellular particles and bacterial cells)
particles made by polymerizing one or more monomers in the presence of magnetically-attractable solids to form directly a synthetic water-insoluble polymeric matrix having the solids uniformly embedded therein
particles of cross-linked protein or polypeptide and a magnetically -responsive material made by combining: an organic solvent solution of a high MW polymer (e.g., polystyrene), a particulate |
| Matrix particles | magnetic material dispersed within a nonmagnetic material | magnetically-responsive material and a polyfunctional cross-linking agent (e.g., polyaldehyde)
hydrophobic vinyl aromatic polymer particles having a mean diameter between 0.03 and 5 microns and a magnetically-charged material in an amount from 0.5 to 50% by weight with respect to the polymer portion of the particles, the magnetically-charged material being dispersed within the polymer particles
a filler selected from the group consisting of a metal, metal alloy, metal oxide, metal salt, metal sulfide, pigment and metallic chelate compound, and an oleophilic surface layer upon the filler, and a layer of polymer upon the oleophilic-surfaced filler |

Magnetic labels formed as matrix or composite particles may optionally include additional coatings or layers of magnetic or nonmagnetic materials or mixtures thereof. Matrix compositions can be made by any suitable means including, but not intended to be limited to, the polymerization of the magnetically-attractable material with the selected monomer, the swelling of the matrix material with the introduction of the magnetically-attractable material into pores within the matrix, and the like. The matrix can include, for example, organic and inorganic materials such as glass, cellulose, synthetic polymer materials, agarose, and the like. Suitable polymer materials include, but are not intended to be limited to, polymers of styrene; substituted styrenes; naphthalene derivatives; acrylic and methacrylic acids; acrylamide and methacrylamide; polycarbonate; polyesters; polyamides; polypyrrole; aminoaromatic acids; aldehydes; proteinaceous materials such as gelatin, albumin and the like; polysaccharides such as starch, dextran and the like; and copolymers of polymeric materials. The polymer may also be used in an admixture with an inert filler or may include an absorbent material.

Generally, the magnetic particles used in the present invention are substantially spherical in shape, although other shapes are suitable and may be advantageous in some circumstances. Other possible shapes include, but are not intended to be limited to, plates, rods, bars and irregular shapes. The diameter of the magnetic label can preferably range from between about 0.01 microns ($\mu$m) and about 1,000 $\mu$m, more preferably from between about 0.01 $\mu$m and about 100 $\mu$m, and most preferably from between about 0.01 $\mu$m and about 10 $\mu$m. As it will be appreciated by those skilled in the art, the composition, shape, size, and density of the magnetically-attractable material may vary widely and a label can be selected based upon such factors as the analyte of interest and the desired assay protocol.

According to one embodiment of the present invention, the magnetic particles can be selected to have a specific gravity so as to tend to be suspended within the reaction mixture thereby enhancing the reactivity of the binding member. Generally, small magnetic particles with a mean diameter of less than about 0.03 $\mu$m (300 Å) can be kept in solution by thermal agitation and do not spontaneously settle. In alternative embodiments, the magnetic particles can be selected to have a specific gravity so as to tend to settle in the reaction mixture thereby enhancing the reactivity of the binding member with the immobilized reagent on the solid phase. Generally, large magnetic particles having a mean diameter greater than about 10 microns can respond to weak magnetic fields. Although large or dense labels may be used, such labels may require that the reaction mixture be stirred or agitated during the incubation steps to inhibit settling of the particles. In another embodiment, the magnetic particles can be selected to remain dispersed in the reaction mixture for a time sufficient to permit the required binding reactions without the need for a stirring or mixing means.

In forming the magnetically-labeled reagent, the attachment of the binding member to the magnetically-attractable material may be achieved by any suitable attachment or coupling means including, but not intended to be limited to, adsorption, covalent bonding, cross-linking (chemically or through binding members), a combination of such attachment means, and the like. Typically, coupling groups and coupling or linking agents are selected so that the binding activity of the binding member is not substantially modified or destroyed upon attachment to the label. The quantity of binding member which may be attached to the magnetically-attractable label is largely dependent upon its concentration, the conditions used, and the amount of and nature of the available functional groups on the magnetically-attractable label or coupling agent.

Preferably, the binding member is covalently bonded to the magnetically-attractable label, and the covalent bond may be formed between one component and a chemically active form of the other component. For example, an active ester such as N-hydroxysuccinimide can be introduced into one component and allowed to react with a free amine on the other component to form a covalent coupling of the two. Other examples include, but are not intended to be limited to, the introduction of maleimide to one component which is then allowed to react with endogenous or introduced sulfhydryl moieties on the other component; the oxidation of endogenous or introduced carbohydrate groups on one component to form aldehydes which can react with free amines or hydrazides on the other component; where the magnetically-attractable label includes a polymer coating or matrix, the polymer may be selected so that it contains, or can be provided with, suitable reactive groups such as, for example, azide, bromoacetyl, amino, hydroxyl, sulfhydryl, epoxide, carboxylic or other groups to facilitate the attachment of the binding member; and the like. Suitable reagents as well as conjugation techniques for synthesizing the magnetically-labeled reagent are well-known to those skilled-in-the-art. It will be understood, of course, that the methods of synthesizing a magnetically-labeled reagent are not intended to limit the invention.

The solid phase material and solid-phase reagents can generally comprise nonporous materials including, but not intended to be limited to, polymers such as, for example, styrene; substituted styrenes; naphthalene derivatives; acrylic and methacrylic acids; acrylamide and methacrylamide; polycarbonate; polyesters; polyamides; polypyrrole; polypropylene; latex; polytetrafluoroethylene; polyacrylonitrile; polycarbonate; glass or similar materials; aminoaromatic acids; aldehydes; proteinaceous materials such as gelatin, albumin and the like; polysaccharides such as starch, dextran and the like; and copolymers of polymeric materials. Such materials can take the form of particles, beads, tubes, slides, tapes, webbing, plates or wells. Thus, the solid phase can be the "reaction vessel" in which the binding assay takes place. For example, the solid phase can be a microtitre well, or it can be a material or materials contained within the reaction vessel, such as, for example, a bead within a test tube.

The solid phase material can also be any suitable chromatographic, bibulous, porous or capillary material. Accordingly, the solid phase material can include, but is not intended to be limited to, a fiberglass, cellulose or nylon pad for use in a flow-through assay device having one or more layers containing one or more of the assay reagents; a dipstick for a dip and read assay; a paper, nitrocellulose or glass fiber test strip for chromatographic or thin layer chromatographic techniques in which one or all of the reagents are contained in separate zones of a single strip of solid phase material; or any absorbent material well known to those skilled in the art.

As further examples, natural, synthetic or naturally occurring materials that are synthetically modified, can be used as a solid phase material. Examples of such materials include, but are not intended to be limited to, polysaccharides such as cellulose materials including paper and the like and cellulose derivatives such as cellulose acetate and nitrocellulose; silica; silicon particles; inorganic materials such as deactivated alumina, or other inorganic finely divided material uniformly dispersed in a porous polymer matrix, with polymers such as vinyl chloride, vinyl chloride polymer with propylene, and vinyl chloride polymer with vinyl acetate; naturally occurring and synthetic cloth such as cotton, nylon and the like; porous gels such as silica gel, agarose, dextran, gelatin and the like; polymeric films such as polyacrylates and the like; protein binding membranes; and the like. The solid phase may also comprise microparticles which can be selected by one skilled in the art from any suitable type of material including, but not intended to be limited to, polystyrene, polymethylacrylate, polyacrylamide, polypropylene, latex, polytetrafluoroethylene, polyacrylonitrile, polycarbonate, glass, and the like.

While the solid phase material preferably has a reasonable strength, or such strength can be provided by means of a support, it preferably does not interfere with the production of a detectable signal. It will be understood, of course, that the solid-phase material is typically nonmagnetic or, if magnetic, that its magnetic contribution to the assay is correctable by, for example, positioning such material in a manner where it is not affected by a magnetic field or such material can be demagnetized. The means of attaching a binding member to a solid phase to thereby form a solid-phase reagent, encompasses both covalent and non-covalent means which have been outlined previously with regard to synthesizing a magnetically-labeled reagent. It is generally preferred that the binding member be attached to the solid phase by covalent means.

(b) Assay Methods & Devices

The methods and devices of the present invention may be applied to any suitable assay format involving binding pair members including, but not limited to, those binding members described above. The assay methods of the present invention utilize the response of a magnetically-labeled reagent to the influence of a magnetic field to qualitatively or quantitatively measure binding between binding pair members. According to the present invention, the presence of an analyte mediates whether or not the magnetically-labeled reagent becomes immobilized to a solid-phase reagent. The analyte can thereby control the extent of the magnetically-labeled reagent's response to the influence of a magnetic field. Hence, by measuring the magnetically-labeled reagent's response to the magnetic field, the presence or amount of analyte contained in a test sample can accurately be determined.

The present invention is applicable to various competitive assay formats and sandwich assay formats well known in the art. Various competitive, inhibition and sandwich assays have been described whereby a labeled reagent is partitioned between a liquid phase and a solid phase in relation to the presence of the analyte in the test sample. According to a competitive assay format, a magnetically-labeled reagent can comprise a first binding member (an analyte analog) attached to a magnetically-attractable label, to thereby form a magnetically-labeled reagent. A solid-phase reagent can comprise a second binding member, which is specific for the analyte and analyte analog, attached to a solid phase. During the course of the assay, an analyte in the test sample and the magnetically-labeled analyte analog compete for binding sites on the solid-phase reagent. Alternatively, the binding member attached to the solid phase may be an analyte-analog selected to compete with the analyte for binding to a magnetically-labeled binding pair member. Hence, the quantity of magnetically-labeled reagent that becomes bound to the solid phase is inversely proportional to the amount of analyte in the test sample.

According to a sandwich assay format, a first binding member is attached to a magnetically-attractable label to form a magnetically-labeled reagent and a second binding member is attached to the solid phase to form a solid-phase reagent. The binding members are selected to directly or indirectly bind the analyte of interest. During the course of the assay, the magnetically-labeled reagent becomes immobilized to the solid-phase reagent by binding the analyte that has bound the solid-phase reagent. Thus, the quantity of magnetically-labeled reagent that becomes bound to the solid-phase reagent is directly proportional to the amount of analyte in the test sample.

According to the present invention, assay protocols may optionally comprise the use of ancillary binding members to indirectly bind the analyte or analyte analog to the magnetically-labeled reagent or to the solid-phase reagent. The ancillary binding member can be attached to a solid-phase reagent or magnetically-labeled reagent before, during or after contacting the solid-phase reagent or magnetically-labeled reagent with the test sample or other assay reagents. In addition, the assay protocols may comprise, for example, contacting the assay reagents and test sample simultaneously to form a reaction mixture, or the assay reagents and test sample can be contacted sequentially, and for a time period suitable for binding to form multiple reaction mixtures.

According to such assay protocols, after a period suitable for binding, the unbound magnetically-labeled reagent can be separated from the bound magnetically-labeled reagent. It will be understood, of course, that the separation of bound and unbound magnetically-labeled reagent may involve the complete removal of the unbound magnetically-labeled reagent from the reaction mixture and/or from that magnetically-labeled reagent which is immobilized to the solid-phase reagent. The separation of bound and unbound magnetically-labeled reagent may also involve the segregation of the unbound magnetically-labeled reagent from the immobilized magnetically-labeled reagent such that the unbound magnetically-labeled reagent remains in the reaction mixture but does not significantly produce a detectable response when the bound magnetically-labeled reagent is placed in the vicinity of a magnetic field. Alternatively, either the unbound or bound magnetically-labeled reagent can be observed for a response to a magnetic field. Further, both the unbound and bound magnetically-labeled reagents can be observed for a response to a magnetic field whereby a ratio of the partitioning can be observed.

Generally, devices according to the present invention comprise components for performing magnetically assisted binding assays as taught herein. Accordingly, such devices preferably comprise (i) a reaction vessel; (ii) a separation means for separating the immobilized magnetically-labeled reagent from the unbound magnetically-labeled reagent; (iii) a magnetic field generator means for the application of a magnetic field to the magnetically-labeled reagent; and (iv) a measurement means to assess the effect of the magnetic field generated by the magnetic field generator means on the magnetically-labeled reagent as a measure of the presence or amount of analyte in the test sample.

The reaction vessel can be anything capable of containing the assay reagents disclosed herein and where unbound and immobilized magnetically-labeled reagent can be produced in relation to the amount of an analyte in a test sample. The reaction vessel can comprise any material previously described herein with respect to the solid phase. Moreover, the solid phase or solid-phase reagent can serve as the reaction vessel such as, for example, test-tubes, microtiter wells, tubing, slides and the like.

Separating the bound magnetically-labeled reagent from the unbound magnetically-labeled reagent can be accomplished by any means suitable for partitioning the unbound and bound magnetically-labeled reagent. For example, a vibratory or tilting means could be used to effectuate the separation. Preferably, the magnetically-labeled reagent that is not immobilized to the solid-phase reagent is separated from the solid phase by the application of a magnetic field which is sufficient to move unbound magnetically-labeled reagent, but not the bound magnetically-labeled reagent. For example, the unbound magnetically-labeled reagent may be removed from the reaction mixture by inserting a magnetic probe into the reaction mixture and then removing the probe with any unbound magnetically-labeled reagent that is attracted to that probe. In another embodiment, the unbound magnetically-labeled reagent may be pulled from the reaction mixture by placing a magnet outside of the reaction vessel and moving the magnet along the vessel bottom and/or wall, thereby pulling the unbound magnetically-labeled reagent from the reaction mixture or away from the reagent which is immobilized to the solid phase. In yet another embodiment, a magnetic means may be brought into proximity with the surface of the reaction mixture such that unbound magnetically-labeled reagent is sequestered at the air/liquid interface of the reaction mixture, thereby separating unbound magnetically-labeled reagent from the immobilized reagent. In a further embodiment, the unbound reagent can be moved away from the immobilized magnetically-labeled reagent, and retained in a suitable manner, such that the unbound reagent is retarded from moving back to the site of the immobilized magnetically-labeled reagent.

The magnetic field generator means can be any means for generating a magnetic field which elicits a response from the magnetically-labeled reagent. Preferred magnetic field generator means include permanent magnets and electromagnets. It will also be understood, of course, that the magnetic field generator means may also be used to separate the unbound or free magnetically-labeled reagent from the bound or immobilized reagent.

A magnetically-labeled reagent's response to a magnetic field can be manifested in many measurable forms including a resulting force or movement of the reagent such as, for example, an apparent weight change of the reagent, a displacement of the reagent, a mass change of the reagent, and the like. It will be understood, of course, that these manifestations can be measured directly by detecting the manifestations of the magnetically-labeled reagent, or the manifestations can be measured indirectly by detecting the magnetically-labeled reagents effect on, for example, the solid phase, the solid-phase reagent or the magnetic field generator means. The influence of the magnetic field upon a magnetically-labeled reagent may be observed or detected and measured by any means suitable for directly or indirectly measuring the magnetically-labeled reagent's response to the magnetic field. For example, a change in the apparent weight can be detected and measured by a balance; a change in apparent mass can be detected and measured by a balance or a resultant change in frequency of a quartz crystal; a displacement can be detected and measured by an optical sensor means to assess the magnitude of a change from an initial position to a subsequent position assumed by the magnetically-labeled reagent, solid-phase reagent or solid phase; a movement can be detected and measured by motion detection means to assess movement, such as, for example, a piezoelectrical film, or a coil such as, for example, a susceptometer which can create a field that is measurably disrupted by the presence and/or movement of magnetic material; and a change in the amount of stress can be detected by incorporating stress sensitive materials into a vessel or solid-phase material such that upon the application of a magnetic field the change in stress would be detectable. It will be understood, of course, that depending upon the particular assay, it may be preferred to detect, directly or indirectly, the unbound magnetically-labeled reagent's, the bound magnetically-labeled reagent's or both the bound and unbound magnetically-labeled reagent's response to the magnetic field. It will also be understood, of course, that a wide variety of instruments can be used to detect mass changes, position changes, movements, weight changes, force changes, magnetic susceptibility, induction and the like; all of which result from the interaction between a magnetic field and the magnetically-labeled reagent.

While various devices and assay protocols are contemplated by the present invention, the following protocols represent examples, and are not intended to be limited to, two sandwich assay formats using the magnetically assisted detection of a magnetically-labeled reagent of the present invention. In this regard, the following protocols, and protocols contemplated by the present invention, can be performed in any order of steps or, alternatively, in a simultaneous manner.

Protocol A 1) a first binding member selected to bind the analyte is attached to a magnetically-attractable label to form a magnetically-labeled reagent;
2) a second binding member selected to bind a second binding site on the analyte is attached to a solid phase to form a solid-phase reagent;
3) a test sample is contacted with the solid-phase reagent to form a first reaction mixture whereby the analyte becomes bound to the solid-phase reagent;
4) the first reaction mixture is contacted with the magnetically-labeled reagent to form a second reaction mixture whereby the magnetically-labeled reagent becomes immobilized upon the solid-phase reagent by binding the captured analyte (the proportion of magnetically-labeled reagent that becomes bound to the solid-phase reagent is directly related to the amount of analyte in the test sample);
5) the unbound magnetically-labeled reagent is removed from the second reaction mixture;
6) the solid-phase reagent and the magnetically labeled reagent bound thereto is placed on a detection means;
7) the second reaction mixture is exposed to a magnetic field such that a magnetic force is exerted on the magnetically-labeled reagent immobilized upon the solid phase, the influence of this force is manifested by the captured magnetically-labeled reagent and the degree of the manifestation is determined by the detection means; and
8) the measurable degree of the manifestation provides a measure of the quantity of the magnetically-labeled reagent bound to the solid phase.

Protocol B 1) a first binding member selected to bind the analyte is attached to a magnetically-attractable label to form a magnetically-labeled reagent;
2) a second binding member selected to bind a second binding site on the analyte is attached to a solid phase to form a solid-phase reagent;
3) a test sample is contacted with the solid-phase reagent to form a first reaction mixture whereby the analyte becomes bound to the solid-phase reagent;
4) the first reaction mixture is contacted with the magnetically-labeled reagent to form a second reaction mixture whereby the magnetically-labeled reagent becomes immobilized upon the solid-phase reagent by binding the captured analyte (the proportion of magnetically-labeled reagent that becomes bound to the solid-phase reagent is directly related to the amount of analyte in the test sample);
5) the solid-phase reagent and magnetically labeled reagent are placed on a detection means;
6) the second reaction mixture is exposed to a magnetic field such that a magnetic force is exerted on the magnetically-labeled reagent, and the influence of the magnetic field causes the unbound magnetically-labeled reagent to manifest the effect of the magnetic field which is detected by the detection means; and
7) the degree of the manifestation provides a measure of the quantity of the bound magnetically-labeled reagent.

Figure 1:
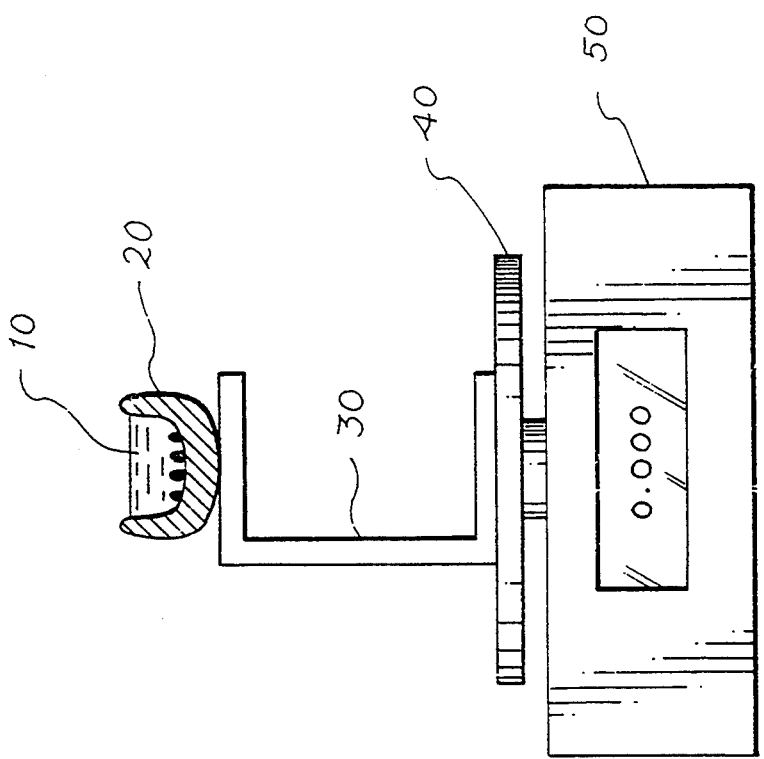
FIG. 1 is a schematic view of the magnetically assisted detection of magnetically-labeled reagent using a balance or weighing means.

FIG. 1 and FIG. 2 illustrate a schematic view of the magnetically assisted measurement of the binding of a magnetically-labeled reagent to a solid phase, and substantially follows Protocol A after the unbound magnetically-labeled reagent has been removed from the second reaction mixture and the solid phase has been placed upon a detection means (step 6). As shown by FIG. 1, the solid-phase reagent comprises a well (20) that contains the immobilized magnetically-labeled reagent (10). The well is introduced to the detection means by setting it upon or affixing it to a support means (30). The support means rests upon a balance means (50). On a typical top loading microbalance, the balance has a pan (40) which will receive the support, and once the balance receives the support, or once the support receives the well, the balance can be tared or set to equilibrium (zeroed).

In FIG. 2, a magnet (60) is positioned into or brought into proximity with the vicinity of the well, whereby the magnetic field exerts a force upon the magnetically-labeled reagent immobilized to the solid-phase reagent. The force exerted upon the magnetically-labeled reagent is manifested as an apparent change in the weight of the solid phase which is registered on the scale of the balance means (50). Generally, the magnet is affixed to an arm means (70) which allows delicate adjustments of the movement of the magnet toward and away from the solid phase.

The magnetic field may be provided by means of a permanent magnetic or an electromagnet and may be applied intermittently or continuously. An electromagnetic may be used so that the magnetic field can be turned off and on rather than moving the magnet or the solid phase. An electromagnet can also be computer controlled, thereby providing for fine adjustments to magnetic field strength. Furthermore, an electromagnet can be used to generate an alternating magnetic field which can have the further advantage of causing the mixing of the magnetically-labeled reagent in the reaction mixture if such mixing is desired.

Figure 3:
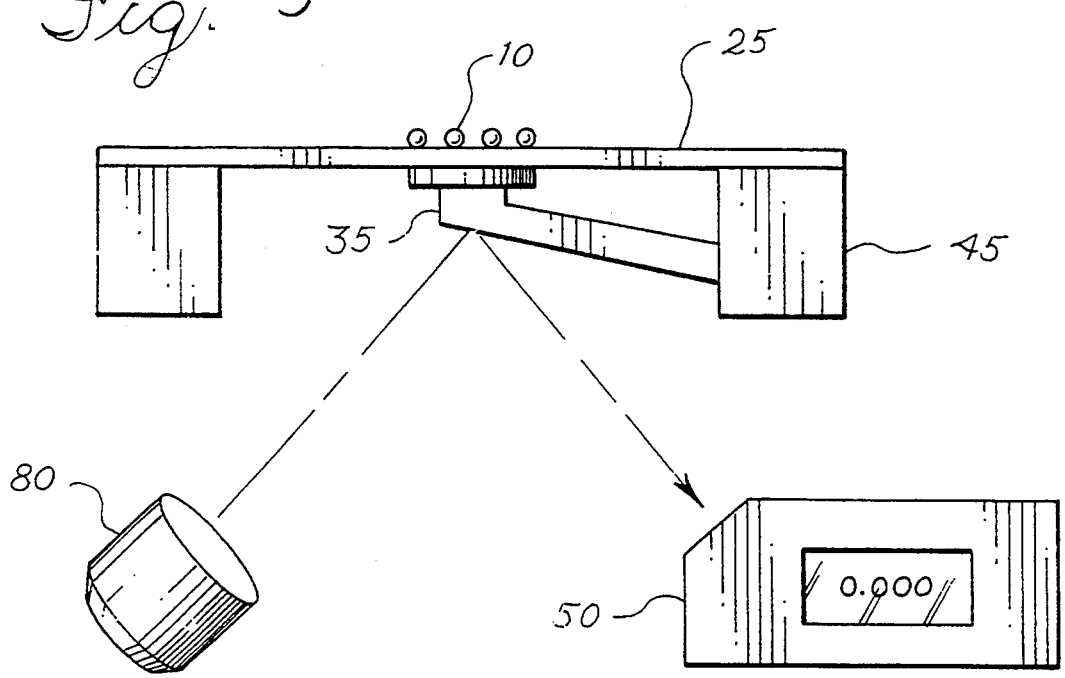
FIG. 3 is a schematic view of the magnetically assisted detection of a magnetically-labeled reagent using an optical sensor means.
Figure 4:
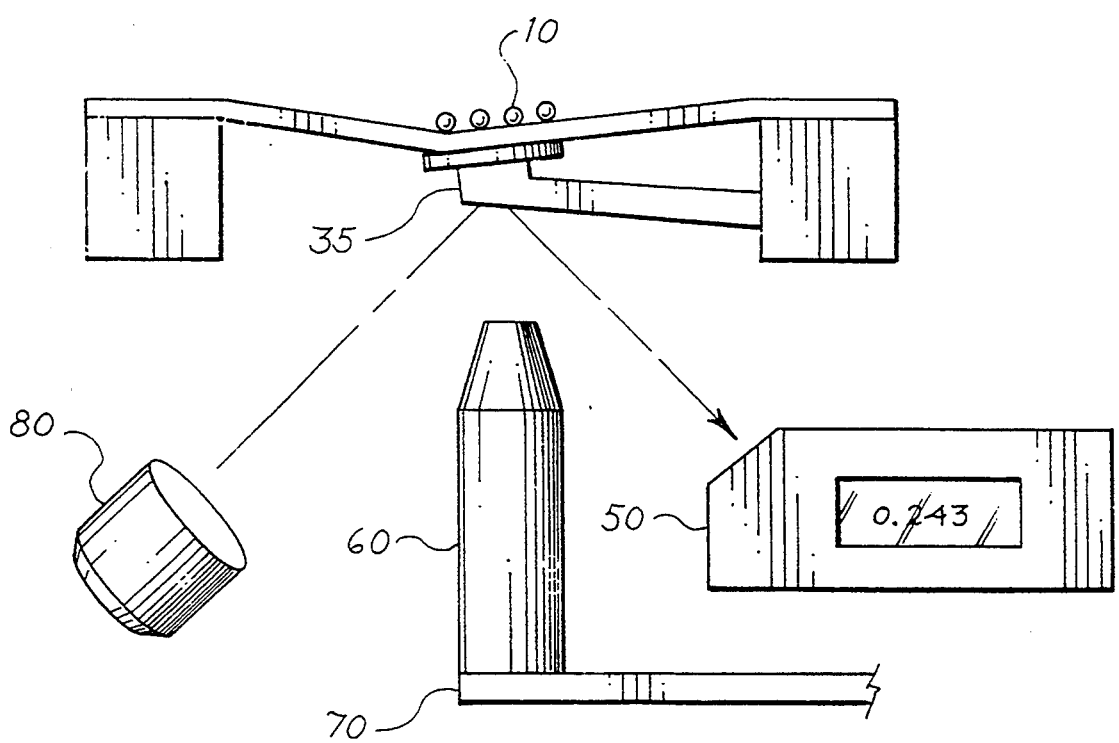
FIG. 4 is a schematic view of an optical sensor means in operation for the magnetically assisted detection of a magnetically-labeled reagent.

FIG. 3 and FIG. 4 illustrate a schematic view of an alternate means for the measurement of the binding of a magnetically-labeled reagent to the solid phase, and substantially follows Protocol A after the unbound magnetically-labeled reagent has been removed from the solid phase and the solid phase has been placed on detection means (step 6). As shown in FIG. 3, the solid-phase reagent comprises a strip of bendable material (25) which has immobilized magnetically-labeled reagent (10) thereon. The bendable material is supported on a foundation means (45). The detection means includes a cantilever beam (35) which contacts the bendable material and deflects in response to any movement of the solid phase. Detection is accomplished by means of a laser light source (80) and an optical sensor means (50). Coherent light from the laser is reflected from the cantilever beam onto the optical sensor. Any deviation in the position of the cantilever beam results in a shift of position or deflection of the reflected light striking the optical sensor, thereby causing a change in its output. The greater the distance traveled by the light, the greater the sensitivity of such a measurement means.

In FIG. 4, a magnet (60) is positioned in proximity to the bendable material, whereby the magnetic field exerts a force upon the magnetically-labeled reagent immobilized on the bendable material. The force exerted upon the bendable material will cause a displacement of the material or a distortion in the shape of the material. The degree of displacement or distortion from the original position of the bendable material is largely dependent upon the amount of magnetically-labeled reagent bound to the solid phase and can be measured by the detection means.

Figure 5A:
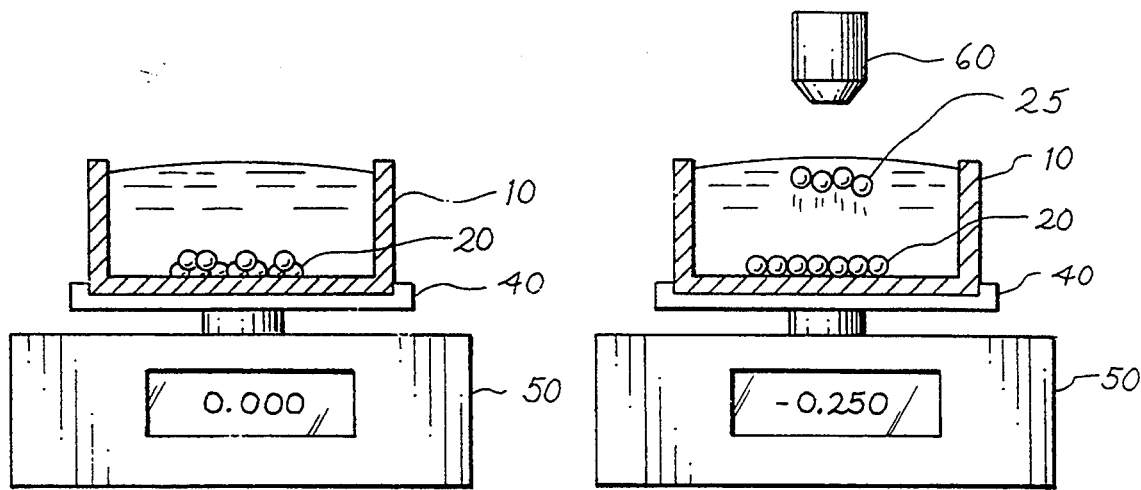

FIG. 5a and FIG. 5b illustrate schematic views of yet another means for the determination of the binding reaction by detecting a force exerted by the unbound magnetically-labeled reagent as a consequence of being exposed to magnetic field. Additionally, the Figures substantially correspond to Protocol B after the solid phase has been placed on the detection means (step 5). As seen in FIG. 5a, the solid phase comprises a well (10) that contains magnetically-labeled reagent (20), at least a portion of which is immobilized in the well. The well is then set upon or affixed to a balance means (50) having a pan (40) which receives the well. Once the balance receives the well, the balance can be zeroed. In FIG. 5b, a magnet (60) is positioned into or brought into proximity with the vicinity of the surface of the well contents whereby the magnetic field exerts a force upon the magnetically-labeled reagent. Under the influence of this force the unbound magnetically-labeled reagent (25) migrates to the air-liquid interface where the magnetic attraction is more intense due to the closer proximity of the magnet. The bound magnetically-labeled reagent resists movement under this level of magnetic field intensity and remains bound through the analyte to the well bottom. The unbound magnetically-labeled reagent at the air-liquid interface strains upward against the surface tension of the liquid surface, causing a change in the apparent weight of the solid phase which is registered as a change of the readout on the scale of the balance means (50). As the magnet is moved closer to the well, the increased intensity of the magnetic field results in a greater change in the apparent weight of the solid phase. As the magnetic field intensity increases, the weaker association of non-specifically bound magnetically-labeled reagent with the well bottom will be overcome, thereby separating it from the specifically bound magnetically-labeled reagent.

The method illustrated in FIG. 5a and FIG. 5b can also be used to determine the strength of the association between binding members and non-specifically bound magnetically labeled reagent. For example, as the magnet is moved closer to the well, the increasing intensity of the magnetic attractive force at the well bottom begins to pull specifically bound magnetically-labeled reagent from the well bottom to the air-liquid interface where it makes a greater contribution to the aggregate upward force on the well.

It is to be understood that since the present invention involves the assessment of the force or movement manifested by the magnetically-labeled reagent, the various detection methods and reagents described herein are readily adaptable to an automated operation or system. However, such automated operation or system is not meant to exclude the possibility that some assay operations in an automated system may be carried out manually.

The present invention will now be illustrated, but is not intended to be limited, by the following examples.

EXAMPLES

Example 1

Magnetically Assisted Magnetic Label Measurement

A plastic support was inserted into the pan receptacle of a electronic balance (Merrier AE 163; Mettier Instrument Corporation, Heightson, N.J.) in a manner illustrated in FIG. 1. The support included a hole in the top cross piece to accommodate a single microtiter well (Nunc snap-apart, eight well module strips; Nunc Incorporated, Naperville, Ill.) so that the bottom of the well would extend below the bottom of the cross piece. A neodymium-iron-boron fixed magnet (Racoma Incorporated, Boonton, N.J.) was placed on the end of a plastic bar attached to the mechanical stage of a microscope so that movement of the mechanical stage allowed the accurate and reproducible positioning of the magnet below the bottom of the suspended microtiter well.

Superparamagnetic particles (polystyrene/vinyl-COOH/magnetite particles; Bang's Laboratories, Incorporated, Carmel, Ind.) were supplied as a 10% (w/v) suspension. This suspension was diluted ten-fold with water to a concentration of 10 milligrams of particles per milliliter. Aliquots ranging from 5–40 microliters (50–400 µg of particles) were pipetted into the microtiter well which was then inserted into the support. The particle suspension was further diluted ten-fold to obtain another set of aliquots containing 5–40 micrograms of particles to assess the response from smaller quantities of particles. A measured quantity of magnetic particles was placed in the microtiter well, and the balance was zeroed with the magnet withdrawn from the vicinity of the well.

In order to measure the force generated upon approach of the magnet to the magnetic particles in the well, the magnet was positioned approximately two millimeters (2 mm) below the well bottom and was moved toward the well bottom in a series of small incremental moves. The balance readout was noted after each movement, and the last reading obtained before the magnet touched the well bottom was recorded. Using this procedure, an average enhancement factor of over 700 was observed, and the effect appeared substantially linear down to at least 20 micrograms of magnetic particles as illustrated by the data presented in Table 2.

TABLE 2

| Weight of magnetically-labeled reagent in a well (micrograms) | Force on the reagent due to magnetic field (micrograms) | Ratio of Weight/Force |
|---|---|---|
| 5 | 4,500 | 900 |
| 11 | 3,300 | 300 |
| 16 | 11,000 | 687 |
| 21 | 13,500 | 642 |
| 27 | 20,000 | 740 |
| 32 | 25,000 | 781 |
| 38 | 25,000 | 658 |
| 43 | 33,000 | 767 |
| 54 | 40,000 | 741 |
| 110 | 97,000 | 880 |
| 160 | 150,000 | 937 |
| 210 | 163,000 | 776 |
| 270 | 130,000 | 481 |
| 320 | 310,000 | 968 |
| 380 | 332,000 | 874 |
| 430 | 275,000 | 640 |

Example 2

Magnetically Assisted Avidin-Biotin Binding Assay

The following reagents and samples were used in a binding assay:

A magnetically-labeled reagent was utilized comprising streptavidin-coated paramagnetic microparticles (Advanced Magnetics, Cambridge, Mass.; average one micron in diameter, with $5 \times 10^8$ particles per mg, supplied as a 5 mg/ml suspension). The binding capacity of the particles was 3.2 micrograms of biotin per milliliter of suspension. Test samples contained various concentrations of biotin in a phosphate buffered saline solution.

A solid phase was utilized comprising snap-apart polystyrene microtitre wells (Nunc 8-well microwell module strips; Nunc Incorporated, Naperville, Ill.) which had been coated with biotinylated bovine serum albumin (biotin-BSA 8.9 moles of biotin per mole of BSA; Sigma Chemical Company, St. Louis, Mo.;). The biotin-BSA was dissolved in phosphate buffered saline (PBS), pH 7.2 to a concentration of 50 micrograms/milliliter, and aliquots (100 µl) were pipetted into each well. Following incubation for one hour at 37° C., the solution was removed from the wells and replaced with 400 microliters of 1% BSA (unbiotinylated) in PBS as an overcoat. Incubation was continued at 37° C. for an additional 45 minutes. The wells were then emptied and washed with PBS using a wash bottle. The overall result of this procedure was to immobilize biotin molecules to the bottom of the microtiter wells (as biotin-BSA) and to inactivate the wells to further non-specific binding of protein by overcoating with unbiotinylated BSA.

The magnetically-labeled reagent was first combined with the test sample, thereby forming a reaction mixture which was incubated for one hour at 37° C. An aliquot (80 µl) of each reaction mixture was transferred to the solid phase, where it was further incubated for one hour at 37° C. to effect avidin-biotin binding. The unbound magnetically-labeled reagent was removed from the reaction mixture by means of magnetic attraction.

Once combined, the free biotin from the test sample proceeded to bind to the available biotin-binding sites on the avidin moieties of the avidin-coated magnetic particles, thereby inhibiting the subsequent capture of the magnetically-labeled reagent by the immobilized biotin on the well bottom. The degree of inhibition depended on the concentration of the free biotin in the test sample. Thus, the amount of magnetically-labeled reagent that was bound by the solid phase was inversely proportional to the amount of biotin in the test sample.

The magnetic responsiveness of the magnetically-labeled reagent bound to the bottom of each well was determined using an apparatus substantially as described in Example 1, above. The weight change due to the magnetic responsiveness of the immobilized magnetically-labeled reagent in each well was recorded as a function of the quantity of free biotin from the test sample present during incubation.

Figure 6:
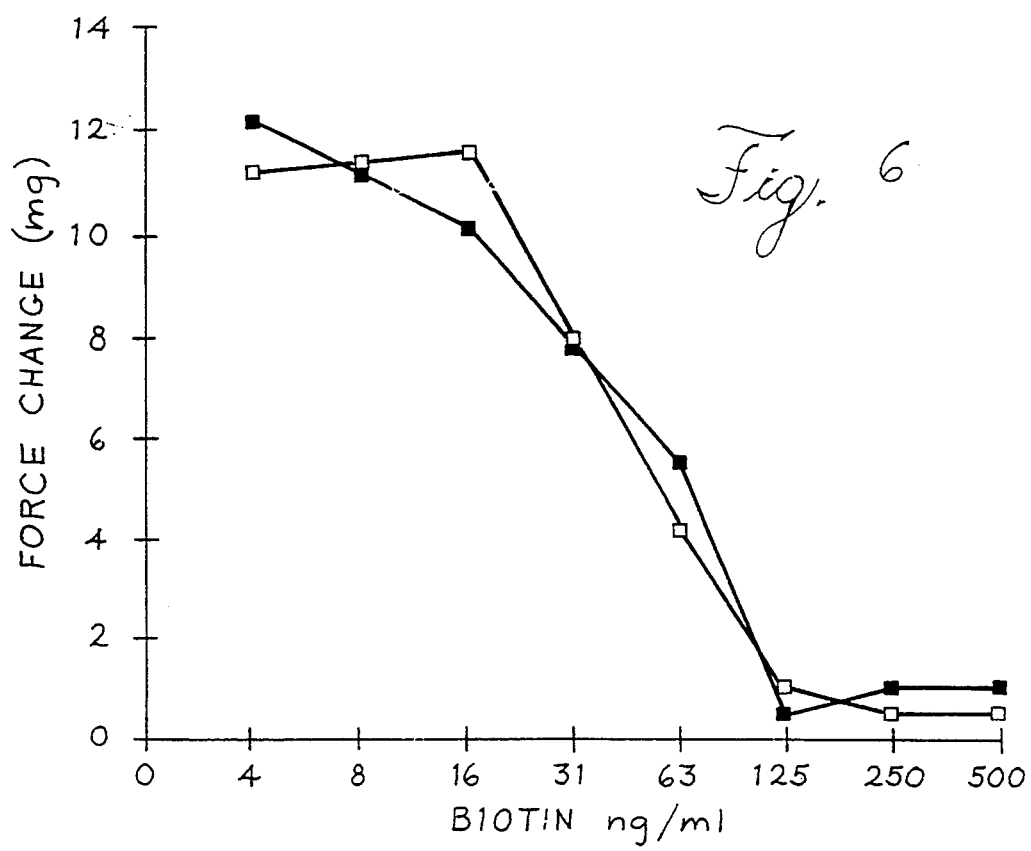
FIG. 6 illustrates the results of a binding assay using a magnetically-labeled reagent as the detectable label.

FIG. 6 illustrates the assay results. The balance means detected a decreasing force change, from 12 milligrams to zero milligrams, as the free biotin concentration in the test sample was increased from 0 nanograms/milliliter to 125 nanograms/milliliter (80 µl assayed). Thus, as the amount of free biotin was increased in a test sample, the amount of magnetically-labeled reagent which bound to the solid phase proportionately decreased, and there was a corresponding decrease in the apparent weight change of that bound reagent upon the application of a magnetic field.

Figure 7:
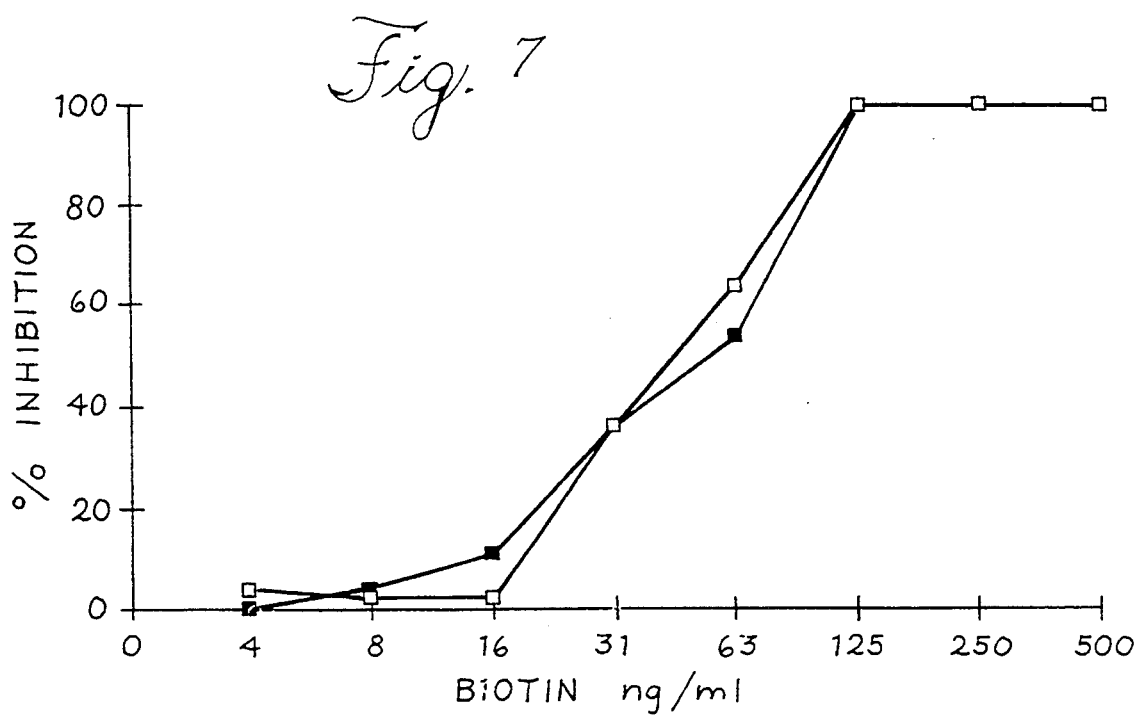
FIG. 7 illustrates the results of a binding assay using a magnetically-labeled reagent as the detectable label, plotted as an inhibition curve.

FIG. 7 illustrates the assay results plotted as a percent inhibition of the magnetically enhanced weight of the captured magnetically-labeled reagent resulting from the presence of free biotin in the test sample. Fifty percent (50%) inhibition was observed at a free biotin concentration of 40 nanograms/milliliter. From these results, it was determined that the assay configuration provided an assay for free biotin in the test sample with a sensitivity in the femtomolar range.

Example 3

Balance Means and Magnetically Assisted Measurements

To further explore the potential of the magnetically assisted magnetic label assay concept, a Cahn Model D-200 electronic microbalance (Cahn Instruments Incorporated, Cerritos, Calif.) was used. This balance consists of a balance beam connected to the rotor of an electric motor. A movement of the beam, as the result of the presence of a weight in one of the hanging pans, is sensed by an optical positioning device, and a current is sent to the motor sufficient to return the beam to its original position. The magnitude of this current is converted by the electronic circuitry of the balance into a weight readout.

An apparatus for precisely positioning a fixed magnet was designed and assembled from three precision positioning tables (Daedal Division of Parker Hannifin Corporation, Harrison City, Pa.). Two of the tables were micrometer adjusted and used to position the magnet in the horizontal X and Y directions. The third table, mounted vertically, was driven by a microstepper motor to control the movement of the magnet in the vertical, or Z direction (Compumotor Division of Parker Hannifin Corporation, Rohnert Park, Calif.). A fixed magnet (Racoma 35; Recoma, Inc., Boonton, N.J.) was attached to the Z table by a bracket which positioned the magnet inside an enclosure that surrounded the balance pans to shield the pans from air currents. The motor movement was controlled by microprocessor circuitry interfaced with a computer. Acceleration, velocity and distance of movement, as well as final position were programmed into the computer such that complex repetitive movements could be executed automatically. A movement of one inch comprised 100,000 microsteps, and controlled movements of one microstep were possible.

The relationship of the magnetic enhancement factor to the quantity of magnetically-labeled reagent was confirmed using the Cahn balance. A ten microliter aliquot of a suspension containing paramagnetic particles as described in Example 1(100 µg/ml) was pipetted onto the balance pan, the balance was equilibrated, the magnet was brought into proximity of the pan and the change in readout was noted. Additional ten microliter aliquots were then added, and the process was repeated until a total of 100 microliters had been added. Table 3 illustrates the relationship between the quantity of magnetically-labeled reagent in the well and the force exerted upon the reagent (measured as an increase in weight) by the magnetic field. As the quantity of magnetic reagent increased, the balance deviation due to the magnet movement increased linearly.

TABLE 3

| Quantity of paramagnetic microparticles in well (micrograms) | Balance Readout (mg) | | | |
|---|---|---|---|---|
| | magnet away | magnet close | Difference | Ratio |
| 1 | 8.05 | 8.74 | 0.69 | 690 |
| 2 | 17.68 | 18.70 | 1.02 | 510 |
| 3 | 27.19 | 28.65 | 1.46 | 487 |
| 4 | 36.78 | 38.91 | 2.13 | 533 |
| 5 | 46.18 | 49.09 | 2.91 | 582 |
| 6 | 55.06 | 58.80 | 3.74 | 623 |
| 7 | 63.80 | 68.29 | 4.49 | 641 |
| 8 | 72.39 | 77.70 | 5.31 | 664 |
| 9 | 80.63 | 86.86 | 6.23 | 692 |
| 10 | 88.76 | 95.88 | 7.12 | 712 |

Example 4

Magnetically Assisted Antibody Assay

A magnetically assisted inhibition immunoassay was demonstrated using the following reagents:

(a) A magnetically-labeled reagent was utilized comprising paramagnetic particles (Advanced Magnetics; Cambridge, Mass.) coated with antibody directed against mouse IgG (heavy and light chain) as a one milligram/milliliter suspension ($5 \times 10^8$ particles/ml).

(b) A solid phase was used comprising the wells of a microtitre plate coated with mouse IgG (100 microliters of a 50 µg/ml solution, in a 1% carbonate buffer, pH 8.6). The solid phase was then overcoated with 1% BSA in PBS.

(c) Test samples (80 microliters) contained various concentrations of free mouse IgG in a PBS buffered solution.

The magnetically-labeled reagent was incubated with the antibody immobilized on the solid phase in the absence of free mouse IgG. The magnetically-labeled reagent bound to the solid phase and resisted removal upon application of a magnetic field. The binding of the magnetically-labeled reagent was shown to be specific for the immobilized mouse antibody, because the same magnetically-labeled reagent was removed by the application of the same magnetic field when incubated with a solid phase which had been coated with BSA alone.

When the magnetically-labeled reagent was first incubated with the free mouse antibody, the subsequent binding of the magnetically-labeled anti-mouse IgG to the mouse IgG-coated on the well bottom was inhibited. The quantity of magnetically-labeled reagent remaining bound to the solid phase, after the magnetic separation of unbound magnetically-labeled reagent, was measured by placing the well on a balance pan, zeroing the balance, and then moving the magnet into position.

Figure 8:
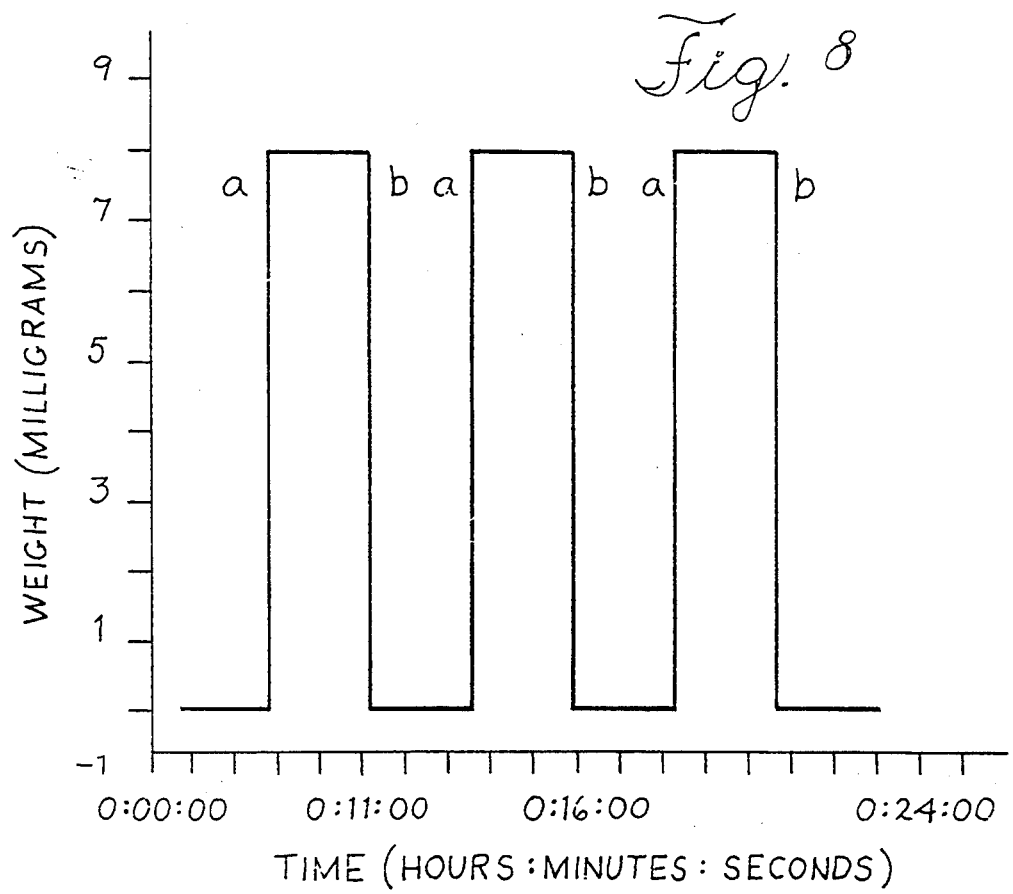
FIG. 8 illustrates the effect of the repeated approach and withdrawal of a magnetic field from a solid phase containing antibody-coated magnetic particles captured by an immobilized antibody.
Figure 9:
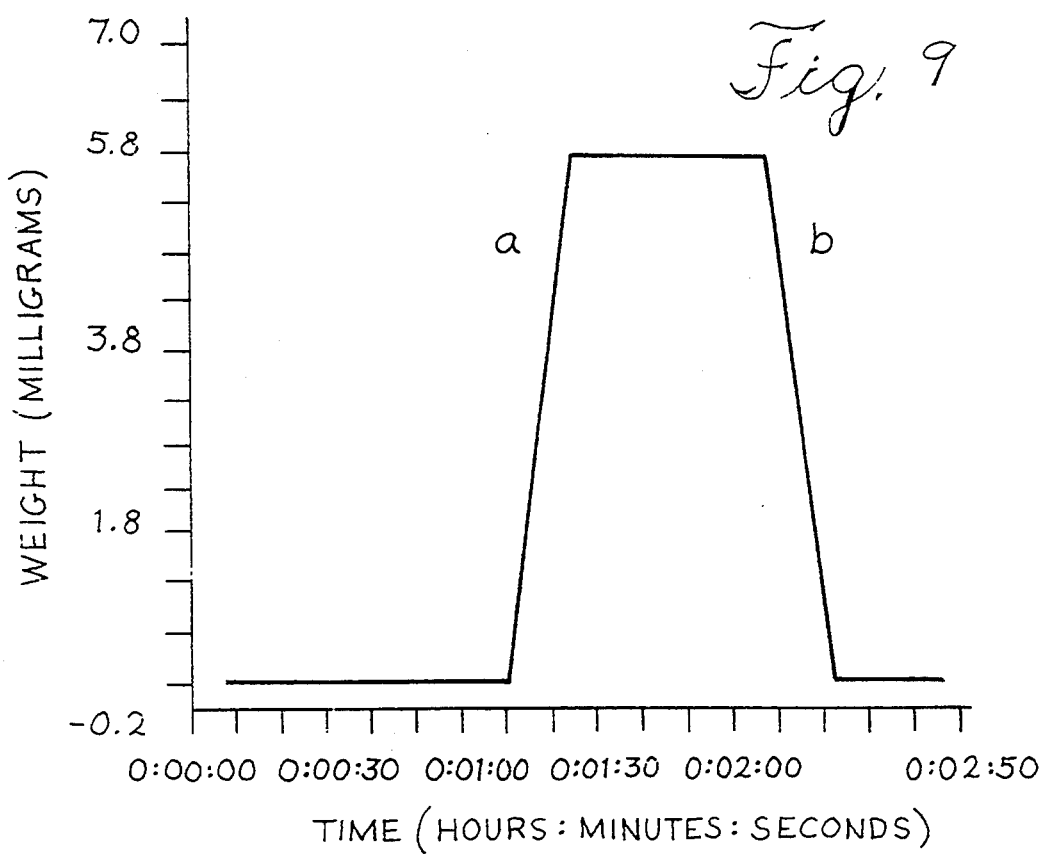
FIG. 9 illustrates a single cycle of the approach and withdrawal of a magnetic field from a solid phase containing antibody-coated magnetic particles captured by an immobilized antibody.

FIG. 8 illustrates the effect of repeatedly moving the magnet first towards and then away from the proximity of the bottom of the well in which there had been no free mouse IgG during incubation, i.e., no inhibition of magnetically-labeled reagent binding to the immobilized antibody in the well bottom; wherein line (a) in FIG. 8 shows the magnetic enhancement of weight upon the approach of the magnetic field and line (b) in FIG. 8 shows the return to the zero point upon the removal of the magnetic field. FIG. 9 depicts the record of a single cycle of the application and withdrawal of the magnetic field under these conditions, which produced an apparent weight change of 5.8 milligrams.

Figure 10:
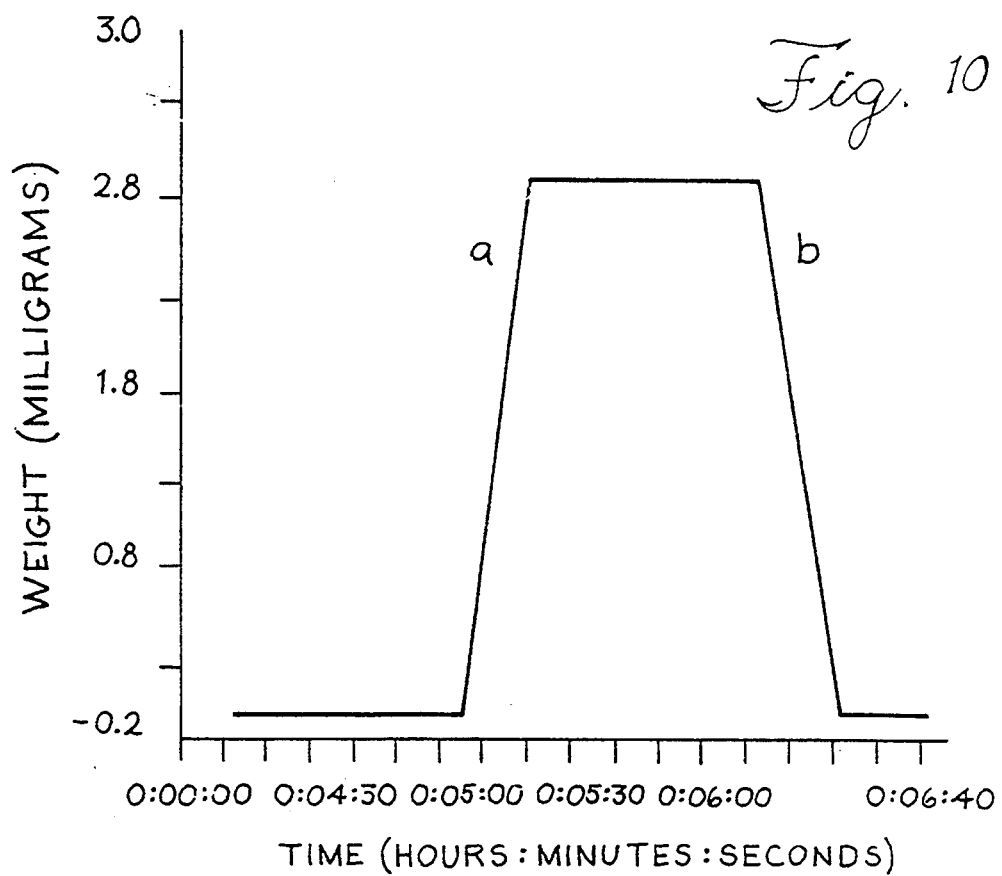
FIG. 10 illustrates the decrease in weight change due to the presence of free antibody during incubation in a system as illustrated in FIG. 9.

The presence of free mouse IgG (at a concentration of 2.5 µg/ml), during the incubation, caused a decrease in the observed effect of the magnetic field. As shown in FIG. 10, incubation of the magnetically-labeled reagent with free mouse IgG at a concentration of 2.5 micrograms/milliliter resulted in a change of apparent weight of only to 2.8 milligrams (note the change in vertical axis units from FIG. 9). The effect of the presence of various concentrations of free mouse IgG during the incubation was determined as percent inhibition of the value obtained in the absence of free mouse IgG.

Figure 11:
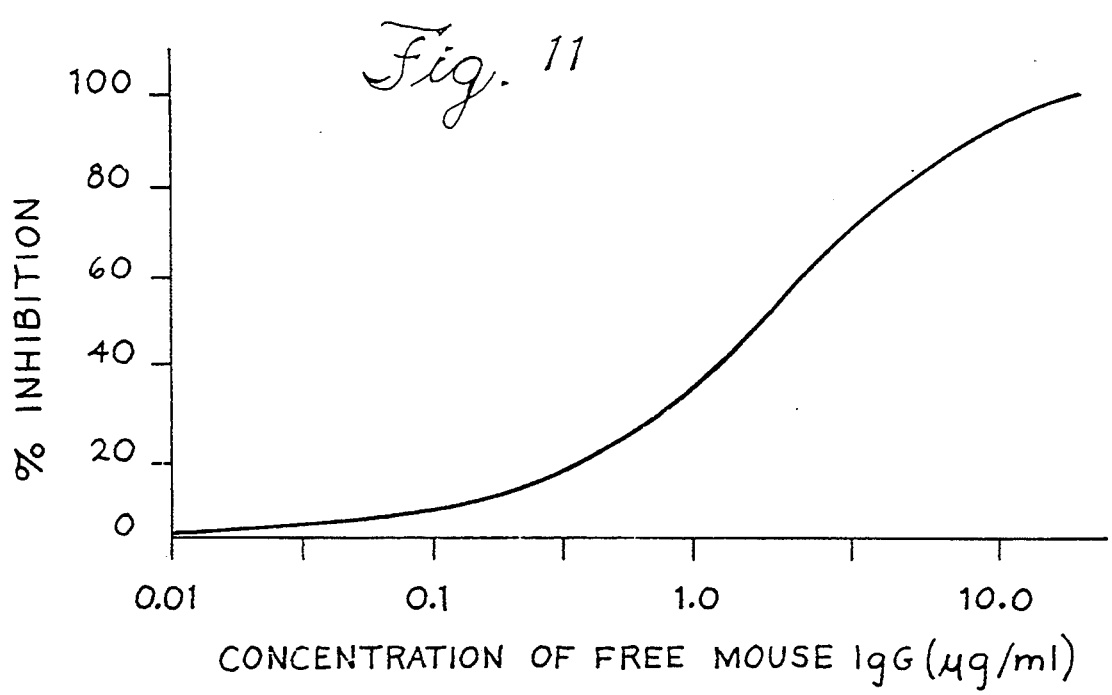
FIG. 11 illustrates an inhibition curve from a magnetically assisted immunoassay.

FIG. 11 illustrates the results which were plotted as a function of free mouse IgG concentration versus per cent inhibition of weight change. The data illustrate a classical inhibition curve with 50% inhibition resulting from the presence of free mouse IgG at a concentration of one microgram/milliliter.

Example 5

Magnetically Assisted Binding Affinity Measurements

The following experiment was performed to measure the binding affinity between a given pair of binding members. The method involved the use of microtiter wells, which had been cut to provide a reduced well wall height of approximately five millimeters, and a magnetic means which approached the wells from above.

The strength of the association between the captured magnetically-labeled reagent and the solid phase was measured. Mouse IgG was immobilized in the well, the well was overcoated with a 1% BSA solution, a suspension of anti-mouse IgG antibody coated magnetic particles was placed in the well, and the reaction mixture was incubated at 37° C. for 1 hour to allow binding to take place.

A magnetic field was moved in discrete steps into proximity with the top of the well, thereby causing a controlled series of increases in the upward attractive force exerted on the magnetically-labeled antibody in the well. FIG. 12 illustrates the procedure, wherein FIG. 12(a) illustrates the magnetically-labeled reagent, some of which is immobilized on the solid phase as a result of a binding reaction, and the balance readout prior to the approach of a magnet to the solid phase. The initial movement (50,000 microsteps) of the magnet toward the surface of the suspension caused that magnetically-labeled antibody which was not bound to the immobilized antibody to migrate to the air-liquid interface of the suspension. As the magnet was moved closer to the surface (in 5,000 microstep movements) there was a corresponding increase in the attractive force upon the free particles resulting in an observable decrease in the weight of the vessel with each discrete movement, as shown in FIG. 12(b). The free particles collected at the interface exerted an upward force against the surface tension of the liquid surface, thereby causing an observable decrease in the apparent weight of the well. The decrease in weight was determined by a balance means substantially in accordance with the method described in Example 1, above. The magnetically-labeled antibody which was bound to the immobilized antibody on the well bottom also exerted an upward force in the magnetic field. The force exerted by the bound reagent, however, was much less than that exerted by the free reagent at the surface due to the greater distance of the bound reagent from the magnet. As the magnet approached the top of the well, thereby causing the upward force on the magnetically-labeled antibody to increase, the magnetically-labeled antibody that was bound to the immobilized binding member on the well bottom began to dissociate from the well bottom and migrate to the liquid surface, as shown in FIG. 12(c).

Figure 13:
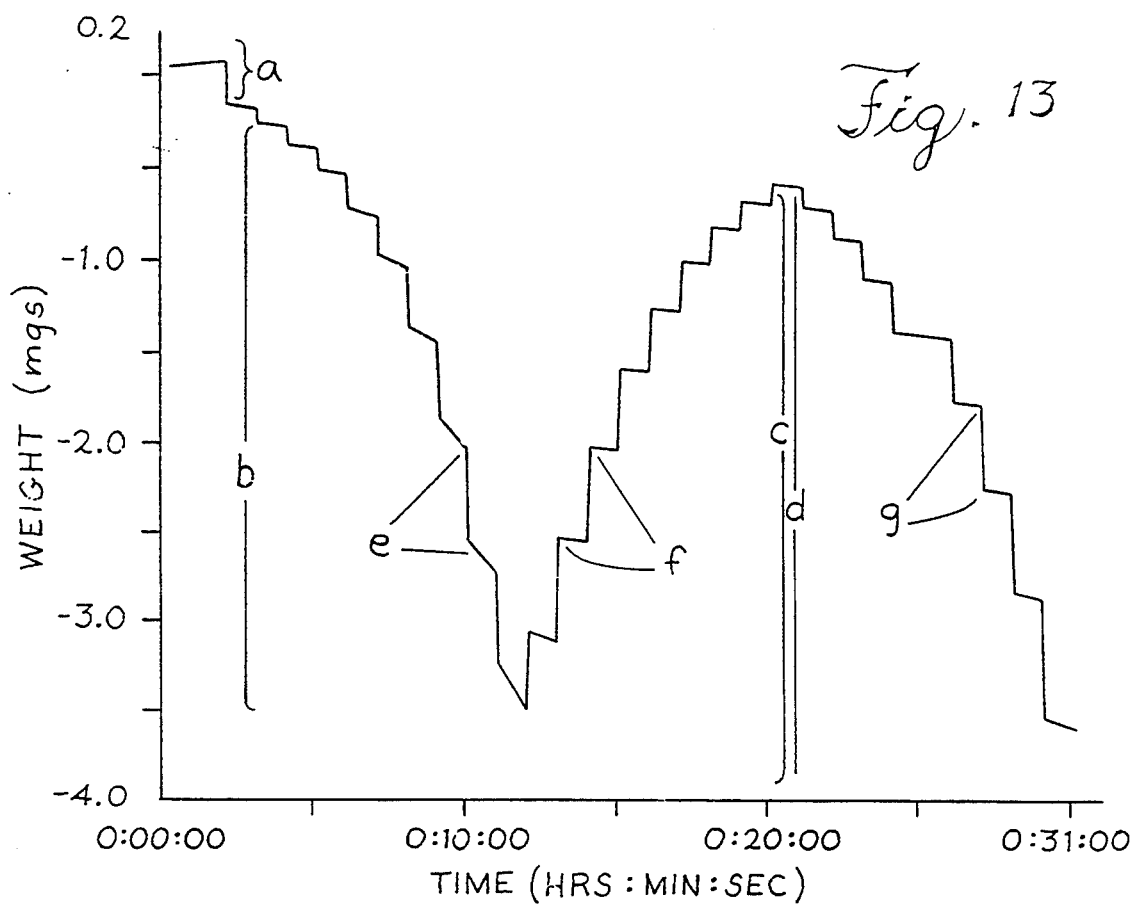
FIG. 13 illustrates an instrument tracing of the weight changes resulting from the approach of a magnet to the top of a vessel containing unbound and immobilized magnetically-labeled reagent.

FIG. 13 illustrates the measurement of the association force of the magnetically-labeled reagent and the solid phase. During the initial 50,000 microstep movement [FIG. 13(a)] of the magnet toward the top of the well, the attractive magnetic field was relatively weak, and the decreases in apparent weight resulted from the increased upwards force exerted upon the free magnetically-labeled antibody which was collected at the air-liquid surface. As the magnet was moved closer to the surface (in 5,000 microstep movements) there was a corresponding increase in the attractive force upon the free particles resulting in an observable decrease in the weight of the vessel with each discrete movement of the magnet [FIG. 13(b)]. Initially, there was no observed weight change when the magnet was stopped between movements, indicating that no change in particle position was occurring between the changes in magnetic field intensity.

As the magnet approached the top of the well, and the force on the bound particles increased, the magnetically-labeled antibody that was bound to the immobilized binding member on the well bottom began to dissociate allowing the magnetically labeled reagent to migrate to the liquid surface. As the dissociated particles reached the liquid surface, they were in a region of a greater attractive magnetic force, and therefore, these particles exerted a greater upward force on the well. This forced dissociation of the magnetically-labeled antibody from the well bottom, and the subsequent migration to the liquid surface, was manifested as a gradual decrease in well weight between movements of the magnet. The change in apparent weight was seen as a deviation of the weight trace from the horizontal between movements [FIG. 13(e)] of the magnet. As the magnet was withdrawn in a series of discrete movements [FIG. 13(c)] from the proximity of the well, the apparent weight changes between movements reverted to zero [FIG. 13(f)].

When the magnet was again advanced toward the same well 13(d), there was little apparent weight change between the movements of the magnet, demonstrating that all of the magnetically-labeled reagent which would dissociate from the well bottom under a given level of magnetic force had already dissociated during the first approach of the magnetic field [FIG. 13(g)]. Thus, any further changes in apparent weight were mostly due to changes in the magnetic field force on the dissociated magnetic microparticles as the magnet moved, with little contribution due to the further disassociation of magnetically-labeled reagent from the well bottom.

Since it is the binding affinity between the magnetically-labeled reagent and the solid-phase reagent which determines its ability to resist dissociation by the applied magnetic field force, the results demonstrated that the association constants between binding members can be quantitatively determined by means of magnetically assisted magnetically-labeled reagent measurements. The attractive magnetic field intensity required to overcome the association of the binding members is a direct measure of the association constant between the binding members.

Example 6

Magnetically Assisted Binding Measurements of Unbound Reagent

A BSA-coated vessel was incubated with a suspension of anti-mouse IgG-coated magnetic particles at 37° C. for 1 hour. The magnetic response measurements (performed substantially in accordance with the method describe in Example 5, above) revealed a decrease of three milligrams in weight when the magnetic means approached the top of the vessel. A vessel containing the same quantity of anti-mouse IgG-coated magnetic particles, but which also contained immobilized mouse IgG (overcoated with BSA), exhibited less than a one milligram weight change, thereby indicating that enough magnetically-labeled reagent had been captured by the immobilized antibody on the well bottom to decrease by two-thirds the magnetic response measurement due to the unbound magnetic particles which had migrated to the liquid surface.

The addition of free mouse IgG, during the incubation of the magnetically-labeled reagent and the solid phase, was found to inhibit the binding of the magnetically-labeled reagent to the immobilized mouse IgG on the well bottom, thereby allowing the unbound magnetically-labeled reagent to migrate to the liquid surface under the influence of the magnetic field and display a greater magnetic responsiveness. In this way, inhibition immunoassays similar to that shown in FIG. 9–11 could be monitored by apparent weight change caused by magnetic particle levitation, i.e., detection of unbound magnetically-labeled reagent. Because magnetic attraction falls off rapidly with distance (as previously shown in FIG. 13), the movement of the free magnetically-labeled reagent nearer to the magnet greatly enhances its influence relative to that of the bound magnetically-labeled reagent. This permits a determination of the relative degree of magnetically-labeled reagent binding without requiring the removal of the free magnetically-labeled reagent from the well.

Example 7

Magnetically Assisted Binding Measurements in a Two Particle Assay

An alternative assay method can involve the use of a particulate solid phase. The magnetically-labeled reagent comprises a binding member conjugated to a magnetic label having an average diameter of 0.05 microns or less. The magnetically-labeled reagent is mixed with an amount of larger nonmagnetic particles (e.g., polystyrene microparticles, diameter of about 5.0 microns) to form a reaction mixture. An immobilized binding pair member on the surface of the nonmagnetic particles causes the magnetically-labeled reagent to bind to the larger particles in the presence of the analyte.

Following a binding reaction, the application of a magnetic field causes the unbound magnetically-labeled reagent to rapidly migrate toward the magnetic means. The magnetically-labeled reagent that is bound to the more massive nonmagnetic particles migrates at a much slower rate in the magnetic field, thereby providing for the discrimination between bound and free magnetically-labeled reagent. After the separation of the unbound magnetically-labeled reagent, that magnetically-labeled reagent that is bound to the non-paramagnetic particles is subjected to analysis using the magnetically assisted magnetically-labeled measurement methods described above.

Example 8

Magnetically Assisted Binding Assay Using a Suspended Field Generator

According to this example an assay was performed with a magnet attached to the balance means. As shown in FIG. 14, a magnet 60 was suspended from the balance beam 65, of a Cahn Model D-200 electronic microbalance (Cahn Instruments Inc.; Cerritos, Calif.). The sample vessel 20 was placed on a pedestle 30 which was attached to a computer controlled elevator device 80. A cylindrical telescoping housing 85 was also attached to the balance and the elevator to shield air currents. When the sample vessel containing a magnetically attractable label 10 was positioned in the proximity of the magnet, a force was exerted on the magnet as it was attracted to the magnetically attractable label in the vessel. As a result, the apparent weight of the magnet increased and the increase was measured by the balance means. With the magnet attached to the balance, the balance is not disturbed during the changing of the sample vessels and the weight of the magnet is constant when the sample vessel is not in the magnet's proximity. Hence, the balance did not have to be rezeroed between each reading step.

An assay for human thyroid stimulating hormone (TSH) was performed using this arrangement. Antibody which was specific for the beta chain of TSH was dissolved at a concentration of 20 ug/ml in phosphate buffered saline (PBS). Aliquots (100 ul) of this solution were pipetted into Nunc snap-apart microtiter wells (Nunc Inc.; Naperville, Ill.) and then incubated at 37° C. for 1 hr. The well contents were then removed and the wells were overcoated with 300 ul of a 1% solution of bovine serum albumin (BSA) in PBS by incubation at 37° C. for 45 minutes. The BSA solution was removed from the wells and replaced with 200 ul aliquots of the TSH containing standards from the Abbott IMx® Ultrasensitive hTSH kit (Abbott Laboratories; Abbott Park, Ill.) before being incubated at 37° C. for 1 hour. After this incubation, the well contents were removed, the wells were washed with PBS, and 300 ul of a 0.002% suspension of superparamagnetic microparticles (0.8 um in diameter, Bang's Labs, Indianapolis, Ind.) which had been coated with an antibody specific for the alpha subunit of TSH were added to each well. The contents of the well were incubated at 37° C. for 1 hour. During this incubation, the particles settled to the bottom of the well and became bound to the immobilized TSH antigen also located at the bottom of the well. After the incubation, each well was filled above its rim with PBS and a glass cover slip was placed over the top of the well such that no air bubbles were trapped beneath it.

The covered well was then placed on the elevator and brought into the proximity of a ring-shaped magnet which served to attract the particles in the well and cause the unbound particles to move up to the underside of the cover slip. The cover slip was removed while in the proximity of the magnet which caused the unbound particles to be removed with it. The well was then centered above the corner of a rectangular magnet, which served to overcome the association between the bound particles and the well bottom. The result was the accumulation of the particles in a dot in the center of the well bottom. All of the liquid was removed from the well and the well was allowed to dry. The well was then inverted and placed on an elevator below the Cahn balance (as described above) and elevated into proximity of the magnet suspended from the balance beam. Weight deflections caused by the presence of the dried dot of microparticles were recorded and plotted as a function of the amount of TSH antigen contained in the standard which had been incubated in each well.

Figure 15:
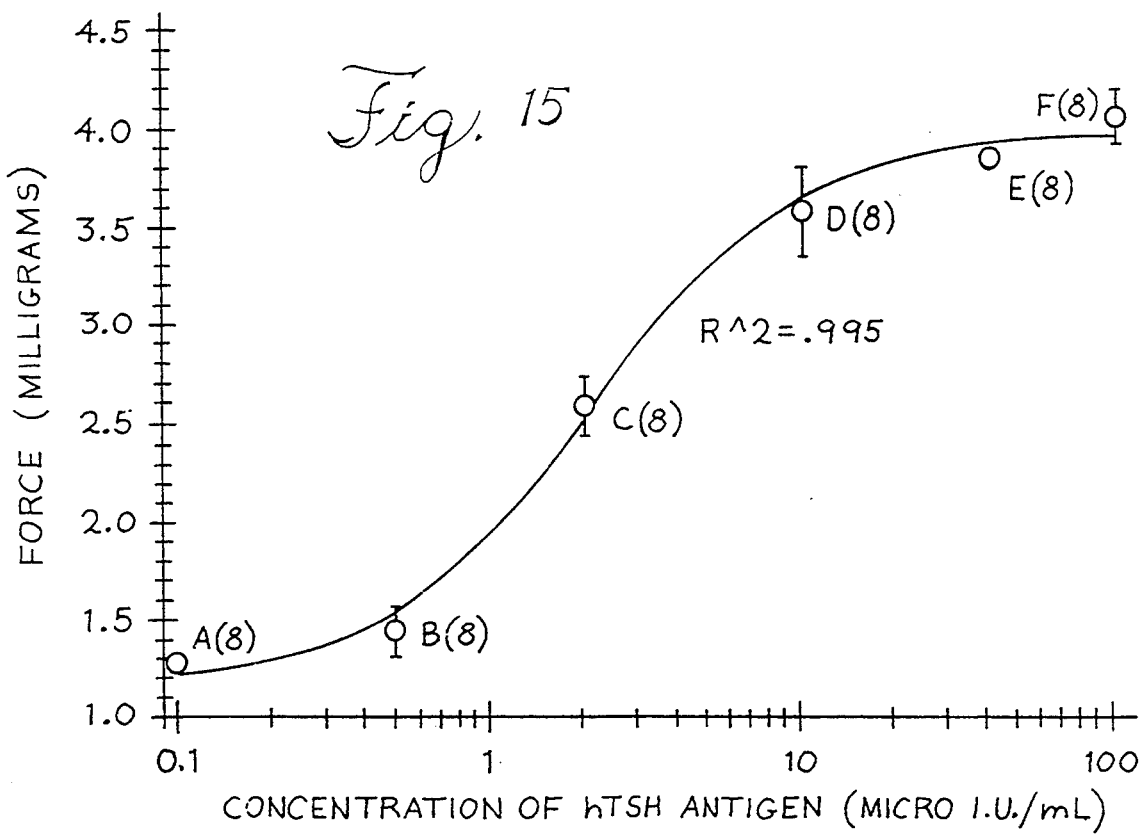
FIG. 15 illustrates the results of a binding assay which was run using an apparatus comprising a field generator means suspended from a balance means.

The data from the experiment is shown below in Table 4 which is also plotted and shown in FIG. 15. The data (shown in Table 4) for each TSH calibrator is an average taken from eight wells.

TABLE 4

| Calibrator | TSH Concentration | Weight Change |
|---|---|---|
| A | 0.0 ul. U/ml | 1.25 mg |
| B | 0.5 ul. U/ml | 1.45 mg |
| C | 2.0 ul. U/ml | 2.6 mg |
| D | 10.0 ul. U/ml | 3.6 mg |
| E | 40.0 ul. U/ml | 3.9 mg |
| F | 100.0 ul. U/ml | 4.1 mg |

Example 9

Figure 16:
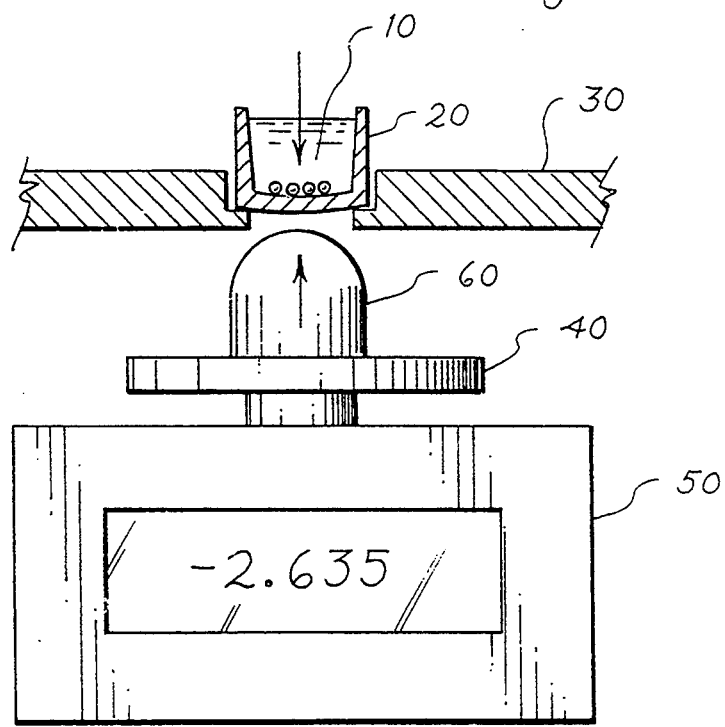
FIG. 16 is a schematic view of the magnetically assisted detection of magnetically-labeled reagent using a field generator means positioned on a balance means.

Magnetically Assisted Binding Assay Using a Field Generator Attached to a Measurement Means In an alternative assay configuration, shown in FIG. 16, a magnet 60 is placed on the pan 40 of a top-loading microbalance 50 to form a magnet-balance configuration. Using support means 30 the bottom of a reaction vessel 20 which contains magnetically attractable material 10 is then positioned in the proximity of the magnet. Apprarent weight changes are then noted. The use of this configuration to analyze the results of an assay described in Example 8 has several advantages. For example, after removal of the unbound magnetically-labeled reagent (as described in Example 8), the well and its contents can be placed directly on the support and the apparent weight change of the magnet noted without removing the well contents or inverting the well.

Example 10

Figure 17A:
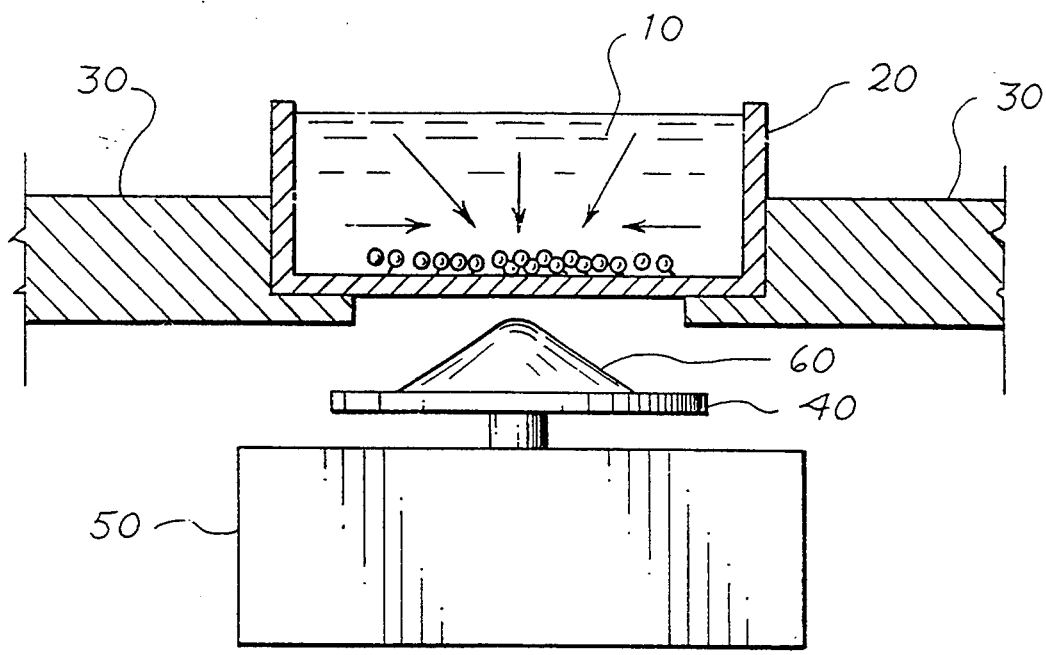
FIGS. 17a–b are sequential schematic views of the magnetically assisted detection of magnetically-labeled reagent using a conical field generator means positioned on a balance means.

Performance of Magnetically Assisted Binding Assays Without Removing Unbound Reagent From the Reaction Vessel The magnet-balance configuration described in Example 9 allows the performance of assays where the unbound particles are not separated from the reaction vessel containing the bound particles. As illustrated in FIG. 17a, a conical magnet 60 is placed on the pan 40 of a top-loading Mettier UMT-2 microbalance (Mettier Instrument Corporation, Heightson, N.J.) 50 to form a magnet-balance configuration. Using support means 30 the bottom of a reaction vessel 20 which contains magnetically attractable material 10 was then positioned in the proximity of the magnet.

Figure 17B:
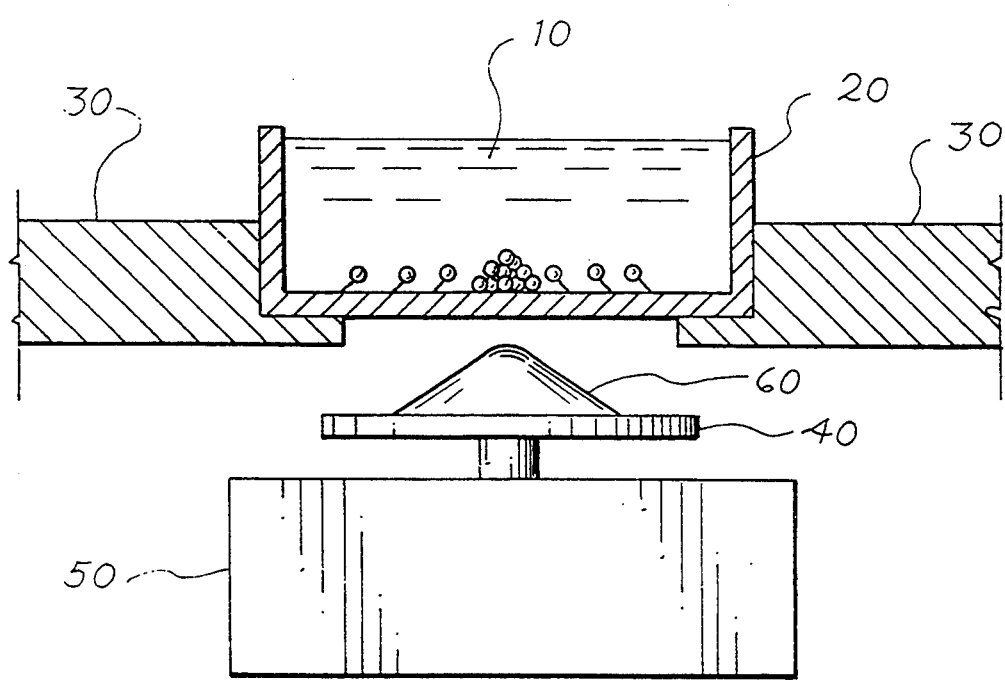
Figure 18:
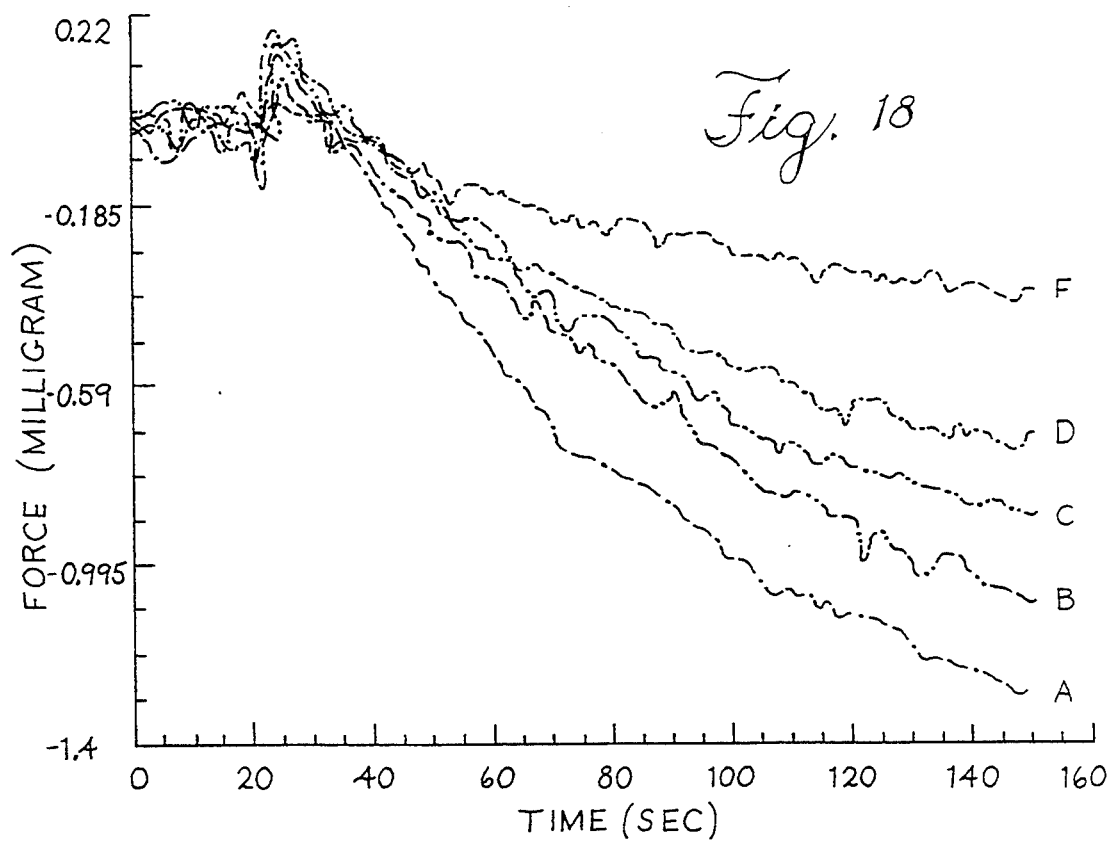
FIG. 18 illustrates the results of a binding assay which was run using an apparatus comprising a conical field generator means positioned on a balance means.

Using such an arrangement, an assay for TSH was performed using wells prepared with the A, B, C, D and F TSH containing standards from the Abbott IMx ® Ultrasensitive hTSH kit (Abbott Laboratories; Abbott Park, Ill.) as described above in Example 8. After the microparticle incubation step (as described in Example 8) the wells were placed in a support 30 which suspended the well over the center of a conical shaped magnet sitting on the pan of a Mettler UMT-2 microbalance (Mettler Instrument Corporation, Heightson, N.J.). As shown in FIG. 17b, when the magnetic field was applied by the magnet 60, the non specifically bound magnetically-labeled reagent migrated to a position in the center of the well 20 above the point of the magnet 60. Because of the shape of the magnetic field generated by the conical magnet 60, particles which migrated to the center of the well exert a much stronger attractive force on the magnet than do the specifically bound magnetically-labeled reagent which has resisted migration. As a result the unbound particles contribute much more to the observed weight change as determined by the balance. The apparent magnet weight changes as a function of time for the above assay are shown in FIG. 18. As shown in FIG. 18, the weight change observed was related to the amount of TSH antigen contained in the standard and thereby contained in the well. Clearly, increasing quantities of antigen increase the binding affinity of the magnetically-labeled reagent for the bottom of the well. For example, the magnetically labeled reagent incubated with the A calibrator (which has no TSH antigen) showed the weakest binding to the well bottom, and therefore, showed the greatest apparent weight change.

It will be appreciated by one skilled in the art that many of the concepts of the present invention are equally applicable to other analytes, binding pair members, assay formats and magnetically-attractable materials. The specific embodiments described are intended as examples rather than as limitations. Thus, the description of the invention is not intended to limit the invention to the particular embodiments disclosed, but it is intended to encompass all equivalents and subject matter within the scope of the invention as described above and as set forth in the following claims.

Example 11

Magnetically Assisted Binding Assay for Alpha Fetal Protein

Figure 19A:
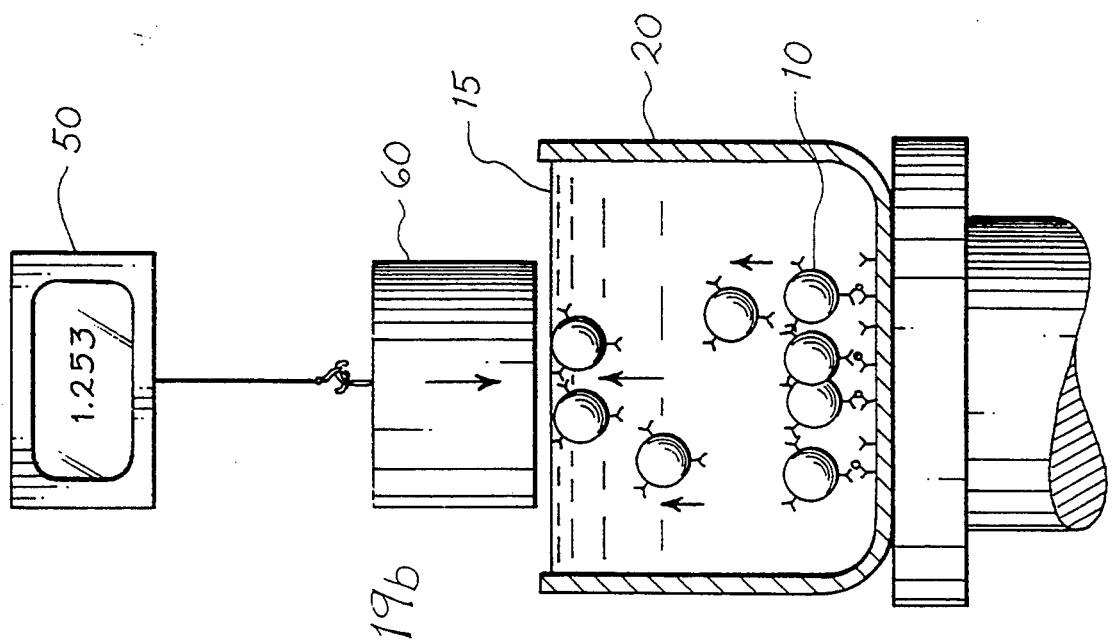
FIGS. 19a–b illustrate Example 11 discussed herein.
Figure 19B:
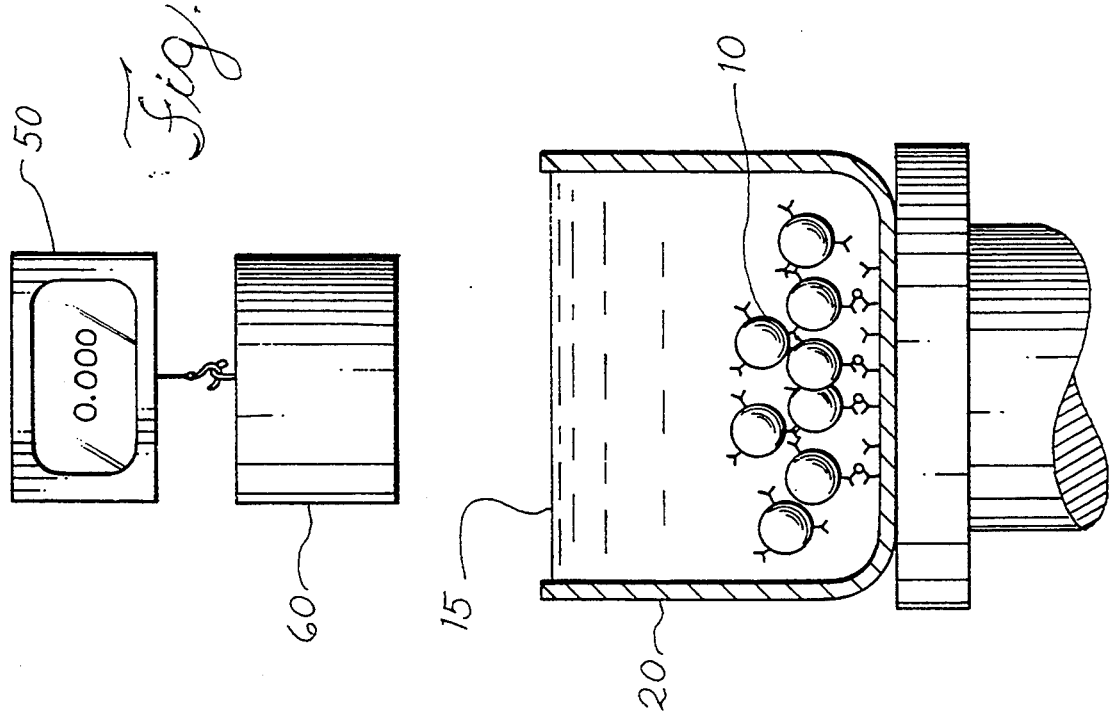

The solid phase (Nunc microtiter wells available from Nunc Inc.; Naperville, Ill., as used in the examples above) was coated with anti-AFP antibody, overcoated with 1% BSA, and incubated with standard amounts of Alapha Fetal Protein (AFP) calibrators from an Abbott AFP IMx ® diagnostic kit (Abbott Laboratories; Abbott Park, Ill.). As illustrated in FIG. 19a and FIG. 19b, the reaction vessel 20 was washed and incubated with a magnetically-labeled anti-AFP antibody reagent 10. Following incubation, a microscope cover slip 15 was placed on top of the well such that the liquid contents of the well contacted the underside of the cover slip thereby leaving no air space. The unbound magnetically-labeled reagent in the well was separated from the bound magnetically-labeled reagent by elevating the reaction vessel in the proximity of a magnet 60 affixed to the beam of a Cahn microbalance 50 (Cahn Instruments Incorporated, Cerritos, Calif.). The unbound magnetically-labeled reagent was pulled to the underside of the cover slip lid of the reaction vessel. In this position, the unbound particles collected on the underside of the cover slip. Because the unbound particles were closest to the magnet, they attracted the magnet most strongly, causing its apparent weight to increase as measured by the balance. This procedure was repeated and the weight change was recorded for each calibrator. The results of the experiment are shown in Table 5.

The results shown in Table 5 show that the higher the concentration of AFP antigen in the calibrator solution, and therefore in the reaction vessel, the smaller the apparent increase in the weight of the magnet. This was due to the magnetically-labeled reagent binding to the AFP antigen bound to the solid phase reagent thereby leaving less unbound magnetically-labeled reagent to migrate to the cover slip and cause the apparent weight change. The magnitude of the apparent weight change of the magnet was inversely proportional to the amount of AFP calibrator in the reaction vessel.

TABLE 5

| AFP Calibrator | AFP (ng/ml) | Balance weight |
|---|---|---|
| A | 0 | 5.8 |
| B | 15.0 | 4.3 |
| C | 50.0 | 2.6 |
| D | 100.0 | 1.2 |
| E | 200.0 | 0.4 |
| F | 350.0 | −0.1 |

Figure 20:
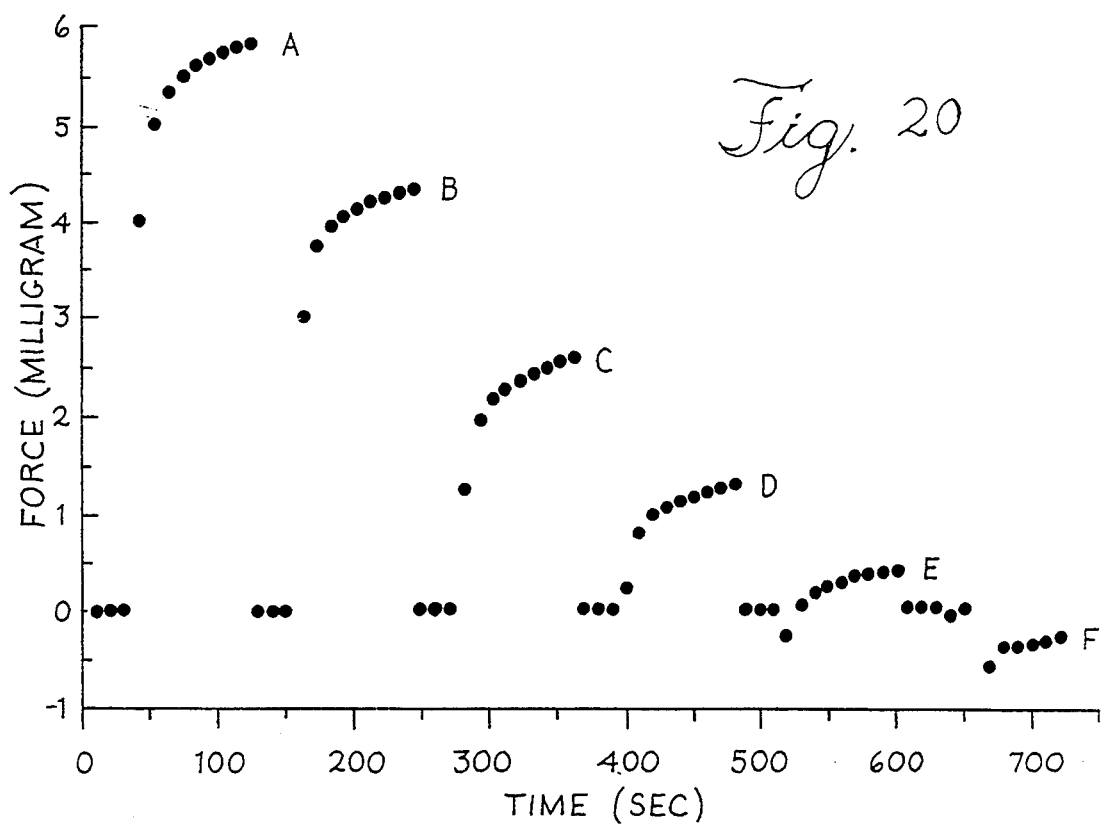
FIG. 20 illustrates rate of apparent weight change during performance of Example 11.

As shown in FIG. 20, the rates of the of the apparent weight change of the magnet during an assay performed in this way can also serve as a measure of the degree of association of the bound magnetically labeled reagent for the solid phase. The rates of change of the apparent weight of the magnet with time are plotted. This approach avoids the necessity of removing the unbound particles from the reaction vessel before the read step, allowing the separation and read step to be performed simultaneously.

Example 12

Measurement of the Rate of Weight Change

The rate of apparent weight change of the magnet during an experiment as described in Example 11 can be controlled by adjusting the distance of the well from the magnet. Movements of the well toward the magnet do not need to be abrupt, but can also be continuous.

What is claimed is:

1. An assay device for determining the presence or amount of an analyte in a test sample, said device comprises:

(a) a reaction vessel wherein unbound and immobilized magnetically-labeled reagent are produced in relation to the amount of said analyte in said test sample;

(b) a separation means, operatively positioned with respect to said reaction vessel, for partitioning said immobilized magnetically-labeled reagent and said unbound magnetically-labeled reagent;

(c) a magnetic filed generator means, operatively positioned with respect to said reaction vessel, for the application of a magnetic field to said magnetically-labeled reagent in said reaction vessel; and (d) a measurement means comprising a balance, operatively positioned with respect to said reaction vessel, to assess the effect of said magnetic field on said magnetically-labeled reagent as a measure of the presence or amount of said analyte in said test sample.

2. The assay device according to claim 1 wherein said separation means comprises a magnetic field generator means which is the same as or different from said magnetic field generator means of (c).

* * * * *